US005288488A

United States Patent [19]

Backman et al.

[11] Patent Number: 5,288,488

[45] Date of Patent: Feb. 22, 1994

[54] METHOD OF CONTROLLING FOLIAR MICROORGANISM POPULATIONS

[75] Inventors: Paul A. Backman; Rodrigo Rodriguez-Kabana; Nancy M. Kokalis, all of Auburn, Ala.

[73] Assignee: Auburn University, Auburn University, Ala.

[21] Appl. No.: 728,316

[22] Filed: Jul. 8, 1991

Related U.S. Application Data

[63] Continuation of Ser. No. 483,505, Feb. 23, 1990, abandoned.

[51] Int. Cl.[5] .................... A01N 63/00; A61K 37/00; C12N 1/00

[52] U.S. Cl. .................... 424/93 D; 424/93 C; 424/93 K; 424/93 M; 424/93 R; 424/DIG. 7; 424/DIG. 8; 435/252.4; 435/271; 435/277; 435/834; 435/839

[58] Field of Search ............ 424/93, DIG. 7, DIG. 8, 424/93 C, 93 D, 93 R, 93 M, 93 K; 435/252.4, 834, 839, 277, 271

[56] References Cited

U.S. PATENT DOCUMENTS

| | | | |
|---|---|---|---|
| 4,764,372 | 8/1988 | Herrnstadt et al. | 424/93 |
| 4,844,896 | 7/1989 | Bohm et al. | 424/93 |
| 4,861,595 | 8/1989 | Barnes et al. | 424/93 |
| 4,886,664 | 12/1989 | Jung et al. | 424/93 |

FOREIGN PATENT DOCUMENTS

| | | | |
|---|---|---|---|
| 0192319 | 8/1986 | European Pat. Off. | 424/93 |
| 2234005 | 10/1987 | Japan | 424/93 |
| 3063373 | 3/1988 | Japan | 424/93 |
| 8800966 | 2/1988 | PCT Int'l Appl. | 424/93 |

OTHER PUBLICATIONS

Bailey, J. E. and Spurr H. W. Fungic Nematic Tests 39:132 (1984).

Cook, R. J. and Baker J. E., in Nature and Practice of Biological Control of Plant Pathogens, pp. 213–218, Am. Phytopatho. Soc., St. Paul, MN (1974).

Bashi, E. and Fokkema, N.J., Trans. Br. Mycol. Soc., 68:17–25 (1977).

Boudreau, M. A. and Andrews, J. H., Phytopath., 77:1470–1475 (1985).

Stu Borman, "Starch-coated pesticide sticks longer on plants," Chemical & Engineering News, vol. 70, No. 31, Aug. 3, 1992.

Chet, I. et al., in *Chitin in Nature and Technology,* R. Muzzarelli et al., eds., Plenum Press, NY, pp. 237–240 (1986).

Backman, P. A., Ann. Rev. Phytopathol. 16:221–237 (1978).

Spurr, H. W. and Knudsen, G. R., in Biological Control on the Phytoplane, C. E. Windels and S. E. Lindow, eds., Am. Phytological Soc., St. Paul, Minn. pp. 45–62 (1985).

*Primary Examiner*—Herbert J. Lilling
*Attorney, Agent, or Firm*—Millen, White, Zelano & Branigan

[57] ABSTRACT

A method of controlling the population of a first microorganism at a foliar locus by preferentially enhancing the population of a second microorganism at said locus, comprises applying to the locus an amount of a durable selective habitat enhancer which substantially preferentially potentiates growth of said second microorganism with respect to said first microorganism. The durable selective habitat enhancer preferably comprises a substantially water-insoluble, weather resistant polymeric substrate and a binder which increases the durability of the habitat enhancer. The second microorganism can be endogenous to the foliar locus or exogenously applied. Chitin and cellulose are preferred habitat enhancers.

20 Claims, 7 Drawing Sheets

METHOD OF CONTROLLING FOLIAR MICROORGANISM POPULATIONS

This application is a continuation of application Ser. No. 07/483,505, filed Feb. 23, 1990 which is now abandoned.

BACKGROUND OF THE INVENTION

This invention relates to a method of controlling the population of a first microorganism at a foliar locus by preferentially enhancing the population of a second microorganism at said locus.

Microbiological plant pathogens and insect pests of plants represent a major source of loss of agricultural productivity throughout the world. Research on the biological control of foliar pathogens is limited when compared with studies concerning this form of control for soilborne pathogens. However, as restrictions on the use of chemical pesticides increase, biological control of foliar pathogens is becoming more important.

The ecosystems which exist on above-ground plant surfaces are complex, and the microbial interactions which occur on it are poorly understood. Plant pathogens and their interactions with the host plant have been influenced under limited circumstances by the population of microbial epiphytes which exist in the foliar phylloplane. The introduction of organisms that exhibit antagonism towards foliar pathogens in this environment has been successful in controlling certain pathogens by several mechanisms, which include direct parasitism of the pathogen by the epiphyte, competition for nutrients and space, the production of antibiotics and/or lytic enzymes by the antagonist, and stimulation of a host resistance response.

Recently, there have been several reported successes using introduced antagonists for the control of foliar diseases in the field. Spurr (1981) used *Pseudomonas cepacia* to inhibit the germination of *Alternaria alternata* and thereby control Alternaria leaf spot of tobacco in field tests by repeated applications over a period of three years. Limited but significant control of Cercospora leaf spot on peanut was achieved in field tests using aqueous suspensions of *P. cepacia* applied to foliage at two week intervals. In later experiments by Bailey and Spurr (1984), *P. cepacia* and *Bacillus thuringiensis* (Bt) were formulated as wettable powders and sprayed onto peanut foliage using xanthan gum, a water-soluble polysaccharide, as a sticking agent. A decrease in Cercospora leaf spot with both *P. cepacia* and Bt was observed. Knudsen and Spurr (1987) formulated several bacteria including *B. cereus* and *P. cepacia* into wettable powders and dusts and applied them to peanuts in the field. Limited control of *Cercospora arachidicola* a was achieved using *P. cepacia* although *B. cereus* survived in greater number, perhaps due to its resistant spores.

An isolate of *Bacillus subtilis* was found to produce a compound that inhibits urediniospore germination in *Puccinia pelargonii-zonalis*, the causal agent of geranium rust (Rytter and Lukezic, 1986). A culture filtrate applied to leaves prior to inoculation with the pathogen reduced the number of rust pustules by 75% compared to controls. The decrease in disease incidence resulting from the application of culture filtrate indicated antibiotic activity. A fluorescent Pseudomonas isolated from the phylloplane of cacao (*Theobroma cacao*) exhibited antagonism to *Monilia roreri in vitro* (Jimenez et al., 1986). When tested in the field it achieved control similar to that obtained with fungicide treatments. Lindow (1983) has successfully used a genetically engineered ice-minus form of *Pseudomonas syringae* to compete with naturally occurring ice nucleation-active bacteria and prevent frost damage. The ice-minus mutant lacks the gene necessary to produce a large surface protein that acts as an initiator for ice crystal formation. Mild frost damage, induced by nucleation-active bacteria, is a precursor for many diseases. Thus, excluding the bacteria from the microenvironment that they normally occupy reduces disease incidence.

The use of fungi as foliar biocontrol agents has received less attention than that of bacteria. There has, however, been success using Trichoderma, which produces an array of potent antibiotics, and has been shown to control Botyris bunch rot and *Phomopsis viticola*, the cause of dead arm disease of grape (Gullino and Garibaldi, 1986). Five applications of Trichoderma spores beginning at dormant bud stage were found to be equivalent to the control obtained by a commercial fungicide.

It is to be noted that in each of these attempts at bacteriological biocontrol of these various diseases, the introduced microorganism showed poor long-term survivability. It is likely that the limited successes achieved utilizing these techniques were probably the result of antibiotics present in the cultural filtrates coapplied to the plants with the microorganisms.

The chemical environment encountered at the surface of a plant may govern the degree of aggressiveness of virulence a pathogen exhibits. One focus of plant disease control using biological agents has been the introduction of organisms capable of preempting the nutrient supply of a pathogen (Baker and Cook, 1974). It has been shown that if an established epiphytic (foliar) ecosystem is continuously supplied with a source of nutrition, it becomes difficult for a newly introduced pathogen to compete and growth of the pathogen is limited accordingly (Warren, 1972).

Bashi and Fokkema (1977) showed that populations of *Sporobolomyces roseus*, an epiphytic yeast, increased when a 2% sucrose solution was applied to leaves as a food base. This indicated that the amount of nutrients present on the leaf was a limiting factor with respect to the growth of these organisms. By monitoring the growth of yeasts on wheat leaves after the application of nutrients, Fokkema et al. (1975) demonstrated that epiphytic bacteria compete effectively for nutrients. They found that yeast populations increased only after antibiotics to limit bacterial growth are applied with the nutrients. The ability of bacteria to utilize certain nutrients varies. Danilewicz (1980) found that epiphytic bacteria capable of utilizing lignin precursors were abundant where the precursors were available. The amount and type of nutrients available on the leaf surface play an important role in influencing the growth of epiphytic bacteria. By studying the effect of nutrients on the epiphytic bacteria of bean leaves, Morris and Rouse (1985) found that the application of low concentrations of nutrients affected the composition of the bacterial community by increasing the proportion of those bacteria able to utilize the nutrient applied.

In regard to disease control, addition of nutrients to aqueous bacterial suspensions enhances survival of the bacterium. Control of northern leaf blight of corn and early blight of tomato was thereby obtained in greenhouse tests (Leben and Daft, 1965). Control of *Phytophthora infestans* on tomato leaves in the greenhouse was achieved using water extracts from composted organic wastes (Weltzien and Ketterer, 1986). Sterile-filtered or heat-treated extracts were ineffective. The use of nitrogen-containing compounds such as urea and lecithin has also been investigated. Burchill and Cook (1971) found that in apple leaves infected with *Venturia inaequalis*, treatment with 5% urea resulted in the fungus producing fewer ascospores. However, this was likely a result of the urea promoting the rotting of the fallen leaves on the ground, thereby suppressing growth of the fungus. Ammonia, the breakdown product of urea, is toxic to some organisms and caused a rapid increase and significant shifts in the microbial populations from gram positive chromogens to gram negative nonchromogens. In vitro tests showed gram positive organisms stimulated growth of the scab fungus, while gram negative organisms inhibited its growth. Boudrea and Andrews (1987) had little or no success controlling *V. inaequalis* by the application of *Chaetomium globosum* ascospores to field-grown trees. The fact that few *C. globosum* ascospores germinate in the absence of nutrients in the form of complex media was suggested as a possible explanation for its poor performance.

With the exception of the lower fungi and yeasts, the most important structural component of the fungal cell wall is chitin (Lopez-Romero and Ruiz-Herera, 1986). In the fungal cell wall, polymers of chitin are embedded in an amorphous matrix composed of β-1,3-glucans and are susceptible to degradation by chitinases in the thin primary wall formed at the growing tip of the hyphae. Ordentlich et al. (1988) in in vitro studies found that chitinolytic enzymes produced by the bacterium *Serratia marcescens* caused degradation of 60% of the hyphal tip cells of *Sclerotium rolfsii*, a soil-borne pathogen.

Chitin has been used as a soil amendment for controlling plant parasitic nematodes and soil-borne pathogens with some success. The addition of chitin to soil stimulates the growth of bacteria, actinomycetes, and fungi capable of producing chitinolytic enzymes (Brown et al., 1979; Godoy et al., 1983; Mitchell and Alexander, 1962). Godoy et al. found that the addition of chitin to soil stimulated the growth of organisms capable of degrading chitin, a component of the middle layer of egg shells in tylenchoid nematodes, through the production of chitinases. The study supported earlier results by Mian et al. (1982) that demonstrated the development of a particular soil microflora in response to the addition of chitin. Many fungi, including species of Aspergillus, Chaetomium, Fusarium, and Verticillium, showed enhanced growth after the addition of chitin to the soil and have been shown to be actively involved in cyst and egg wall degradation of species of Heterodera and Meloidogynee (Godoy et al., 1982; Godoy et al., 1983; Morgan-Jones and Rodriguez-Kabana, 1981; Ownley-Gintis et al., 1982).

In regard to the control of soil-borne fungal pathogens, Chet et al. (1986) have shown that chitin amendments stimulate the growth of the fungus *Trichoderma harzianum* which produces enzymes capable of degrading the cell walls of *Sclerotium rolfsii, Rhizoctonia solani*, and Fusarium spp., giving it great potential as a means for controlling soil-borne plant pathogenic fungi.

Each of the approaches to microbiological biocontrol of plant diseases discussed above has demonstrated only a limited success. In particular, it is noted that long term survival and reproduction of the microorganisms was not shown to be enhanced by these approaches, despite the number of years that biocontrol has been considered an ecologically and commercially important goal.

SUMMARY OF THE INVENTION

One aspect of this invention provides a method of controlling the population of a first microorganism at a foliar locus by preferentially enhancing the population of a second microorganism at said locus, comprising applying to the locus an amount of a durable, substantially water-insoluble, polymeric substrate which is preferentially biodegraded by said second microorganism with respect to said first microorganism, whereby growth of said second microorganism is substantially preferential to that of said first microorganism. In a preferred embodiment, the polymeric substrate comprises a polysaccharide and further comprises a binder which increases the durability of the polymeric substrate. In another preferred aspect, the method further comprises applying an inoculum of the second microorganism to said locus. Preferred polymers serve in this embodiment as food sources for the desirable microflora.

Another aspect of this invention provides a method of controlling the population of a first microorganism at a foliar locus by preferentially enhancing the population of a second microorganism at said locus, comprising applying to the locus an amount of a durable, substantially water-insoluble polymeric substrate effective as a selective habitat enhancer which substantially preferentially potentiates growth of said second microorganism. In a preferred embodiment, the polymeric substrate is a polysaccharide, and further comprises a binder which increases the durability of the polymeric substrate. In another preferred aspect, the method further comprises applying an inoculum of the second microorganism to said locus. Preferred polymers serve in this embodiment as physical protection for the desirable microflora.

Still another aspect of the invention provides a method of enhancing the population of a microorganism at a foliar locus, comprising applying to the locus an amount of a durable, substantially water-insoluble polymeric substrate which is biodegraded by the microorganism, whereby growth of the microorganism is potentiated. In a preferred aspect, the polymeric substrate is applied in admixture with a binder which increases its durability.

A fourth aspect of this invention provides a method of enhancing the population of a microorganism at a foliar locus, comprising applying to the locus an amount of a durable, substantially water-insoluble polymeric substrate effective as a selective habitat enhancer which potentiates growth of said microorganism. In a preferred embodiment, the polymeric substrate is a polysaccharide, and further comprises a binder which increases the durability of the polymeric substrate.

A fifth aspect of this invention provides a durable foliar habitat modifier, comprising (a) a water-resistant, weather resistant polymeric substrate, (b) a binder which increases the durability of the habitat modifier, and (c) a microorganism whose growth is enhanced by the durable foliar habitat modifier. In a preferred aspect, the modifier further comprises one or more of a surfactant, a buffering agent, a dispersant, a humectant, a UV absorber, or an IR reflector.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings wherein.

DETAILED DESCRIPTION OF THE INVENTION

Figure 1:
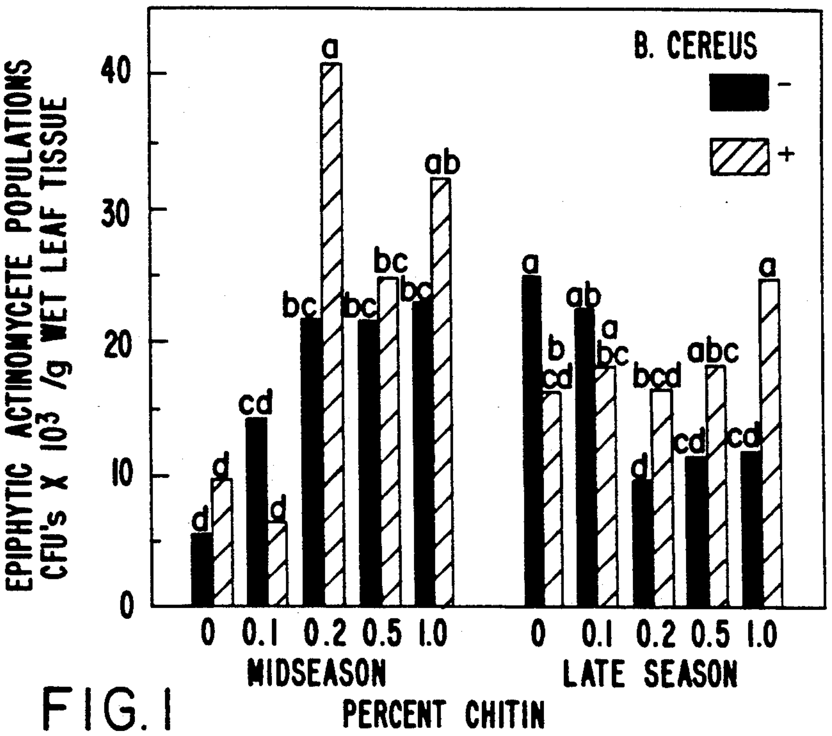
FIG. 1 shows the effects on epiphytic actinomycetes of chitin Formulation with and without the addition of *Bacillus cereus*.

This invention thus provides a preferred method for biological control of pathogens of above-ground plant parts whereby indigenous or exogenously applied organisms are provided with a durable selective habitat enhancer comprising a durable, substantially water-insoluble polymer that serves as a source of food and/or of physical protection. This invention similarly is applicable to methods for biological control employing microbial bioherbicides and bioinsecticides.

Previous attempts at biocontrol failed in part because of a harsh and nonsupportive foliar environment; this disadvantage is overcome by the application of this invention. In the prior art attempts, the preferred species failed to actually thrive and grow stably at the foliar locus. Invariably, the prior art applied microorganisms either alone or in combination with watersoluble amendments, primarily in the form of food supplements. These included water-soluble monomeric sugars, urea, whey, and components of microbiological media which are easily washed off the leaves by water in the form of rain or irrigation. However, the foliar amendments of this invention are durable, so that necessary reapplications of the foliar amendments are infrequent, and are required primarily to cover new growth, with the concomitant reduction in disturbance of the foliar ecosystem, once enhanced, as well as cost reduction.

The mechanism by which the enhancement of this invention occurs can vary widely, including, but not limited to, physical effects such as enhancement of the sheltering aspects of the habitat which favor the preferred species, and metabolic effects such as preferential utilization of the habitat enhancer as a food source.

The mechanism of enhancement of preferential growth of the preferred species, preferably over that of the pathogenic species, may then have its effects through several secondary effects, including, but not limited to, selection pressure resulting from competition for limited resources, production of selective antibiotics, lytic enzymes or toxins by the antagonist, e.g., fungicides, insecticides, phytotoxins, etc., direct parasitism of the pathogen by the preferred species, induction of plant disease, stimulation of the host plant resistance response, etc. No matter what the mechanism is, however, the end result is that the preferred species, by benign competitive antagonism and/or actively detrimental antagonism of the species whose growth is to be controlled, is provided with an environmental selective advantage due to the enhancement of its habitat at the foliar locus. Often, of course, there will be "tertiary" end-result effects flowing from these mechanisms, e.g., enhanced growth of a crop, control or killing of undesired vegetation, etc. Also included in this invention will be instances where the enhanced growth of a desired microorganism and/or the slowed growth or death of an undesired microorganism is the end result. Further included are instances where the end result to be achieved is the enhanced growth of a microorganism, irrespective of any effects on any other microorganism. These effects include production by the preferred species of plant growth hormones and bioinsecticides and detoxification of plant pesticides. Thus, this invention provides a method for control of disease, insects, vegetation, etc., without the application of toxic, persistent or otherwise environmentally undesirable chemicals.

The preferred species may be endogenous to the plant phylloplane, or may be applied to the plant, concurrently or sequentially, with the durable selective habitat enhancer. In either case, the species whose growth is to be preferred may be selected by one of skill in the art from any known species, e.g., one which can antagonize the growth of the plant pathogen (including, for example, an insect or nematode pathogen) which is to be controlled. If the preferred species is one which is already present at the foliar locus, it can be selected by one skilled in the art by knowledge of its presence, and what would provide a selective advantage to it, which, if not known precisely, can easily be determined by routine and conventional screening techniques in view of this disclosure. If the microorganism is to be added exogenously, it may similarly be selected by one of skill in the art by choosing from known species, e.g., antagonists to a pathogen or insect whose growth is to be controlled, or by routinely and conventionally screening known species in order to find a preferred antagonist. Examples of suitable antagonistic species known in the art for antagonizing particular known plant foliar pathogens are shown in Table 1. Other examples of suitable pathogen-antagonist pairs can be found in Rogers, 1989. Previous attempts to use these antagonists to control the cited diseases have had limited success, however, due to the difficulty of maintaining stable populations of the antagonist in the phylloplane, as mentioned.

TABLE 1

| Plant | Pathogen | Antagonist | Reference |
|---|---|---|---|
| Wheat | *H. sativum* | Unk. bacterium isolated from wheat | Simmonds, 1947 |
| Tree stumps | *F. annosum* | *P. gigantea* | Artman, 1972 |
| Tobacco | *A. alternata* | *P. capecia* | Spurr, 1981 |
| Peanut | Cercospora | *P. capecia* | Spurr, 1981 |
| Peanut | Cercospora | *P. capecia* and *B. thuringiensis* | Bailey and Spurr, 1984 |
| Geranium | *P. pelargonii-zonalis* | *B. subtilis* | Rytter and Lukezic et al., 1986 |
| Cacao | *M. roreri* | Pseudomonas | Jimenez et al., 1986 |
| Snap bean | *B. cinerea* | *T. hamatum* | Nelson and Powelson, 1988 |
| Grape | *B. cinerea* and *P. viticola* | Trichoderma | Gullino and Garibaldi, 1986 |
| Corn | "Damping off" | *C. globosum* | Kommedahl et al., 1981 |
| Apple | Apple scab | *C. globosum* | Cullen et al., 1984 |

Other combinations of pathogen and antagonist will be apparent to one of skill in the art, or can be routinely determined by one of such skill. Preferred will be particular strains which can be routinely isolated from known sources or can be purchased from various commercial suppliers.

Suitable microorganisms whose growth is to be enhanced include, but are not limited to, bacteria, algae, yeasts, actinomycetes and fungi having the desired characteristics, e.g., having suitable antagonistic characteristics, including, for example, suitable metabolic pathways for the polymeric substrate, opportune growth characteristics for the particular plant and environment, and production of an appropriate antibiotic or lytic enzyme, elicitor, etc. for the particular pathogen to be controlled. Suitable genera include Chaetomium, which are fungi; Bacillus, which are gram-positive bacteria; Enterobacterium, which are gram-negative bacteria; Curdobacterium, which are Coryneform bacteria; these exemplify a broad range of suitable genera. Other suitable microorganisms whose growth is to be enhanced include, but are not limited to, engineered microorganisms, e.g., derived from the same types discussed above, which are constructed so as to have several concomitant favorable characteristics, as described above, e.g., engineered selective ability to use the amendments of this invention (e.g., to metabolize a particular substrate) and/or engineered ability to produce a secondary effect as discussed above.

Similarly, it is possible to preferentially enhance the growth of microorganisms which produce, or which can be engineered to produce, toxins, for example, Bt (*Bacillus thuringiensis* toxins) in order to kill parasitic plant insects, either by infecting the insects or by poisoning insects which ingest the toxin either by eating the microorganisms themselves or foliar surfaces contaminated with the toxin. Other contemplated equivalents include preferential growth of microorganisms which produce, or are engineered to produce, phytotoxins (biological herbicides) which are directed at selectively killing or inhibiting the growth of the detrimental plants on which they are growing, while selectively not harming other plants, and of microorganisms which produce insecticides, nematicides, elicitors, hormones, e.g., plant growth hormones, etc. Still another possibility is the preferred growth of microorganisms which can detoxify conventional pesticides which may be present on the foliar surface, or on the edible fruits, due to the use of these pesticides in the conventional way. Thus, this aspect of the invention contemplates the preferred growth of pesticide detoxifying microorganisms at various times and for various reasons; for example, just prior to harvesting, so as to decrease the toxic effects of these agents upon the animals eating the plant products. These uses are examples of embodiments wherein the effects on "other" microorganisms may be irrelevant.

As used herein, the terms "foliar" and "phylloplane" relate to all above-ground, aerial parts of the plant, especially the leaves, but also including the shoots, bark, trunk, stems, flowers, pods and fruits. It excludes surfaces contacting the soil; for example, the roots and other underground parts of the plant such as tubers.

Suitable plants to which the durable selective habitat enhancer according to this invention can be applied include any agriculturally important plants, as well as decorative and home garden plants. These include, but are not limited to, monocots, dicots, gymnosperms, evergreens, ferns, mosses and lichens.

More generally, it is possible to use the method according to this invention to treat any above-ground surface to antagonize the growth of undesirable microorganisms. For example, buildings and other surfaces containing habitats consistent with growth, such as grout and metal roofs, metal sculptures, roof tiles, shingles, and swimming pool decks, may be treated with the durable selective habitat enhancer of this invention in order to prevent the growth of undesirable microorganisms such as molds, algae, mosses, lichens and bacteria which cause deterioration or cosmetic damage to these surfaces, etc.

The term "durable" as used herein means long-lasting at the desired site, e.g., weather-resistant and waterresistant, to a sufficient degree that the preferential growth of the selected-for microorganism is of a degree effective to cause the desired end-effect. This desired effect may be, e.g., population disenhancement or suppression of the species whose growth is to be controlled, or population enhancement of a species to be benefitted, or some other secondary or end-result effect as described herein. Population effects will generally be, e.g., about 25-50%, preferably 100%, especially orders of magnitude more or less than the original level (depending on the desired effect). Thus, the desired effect may also be, e.g., the amelioration of disease caused by the microorganism whose growth is to be controlled to acceptable levels, preferably comparable with levels of amelioration achievable with conventional pesticides. Similarly, when the desired effect is insecticidal or herbicidal, "durable" means environment-resistant, e.g., weather-resistant and water-resistant, to a sufficient degree that the preferential growth of the selected-for microorganism is of a degree effective to cause the desired insecticidal or herbicidal effect. In general, as applied to the selective habitat enhancer at the foliar locus, the term "durable" means that the material substantially remains on said locus for, e.g., >1 week, and preferably >2-3 weeks. Even more preferably, the material will not substantially be removed by the natural environment, irrigation, or other erosive events during this time period, or preferably during the entire relevant period of time, e.g., the growing season or the pathogen-sensitive time period for the particular plant in a given year.

The term "selective habitat enhancer" as used herein means an agent which, when applied to a foliar locus, modifies the microfloral environment at said locus such that the ecology of the microfloral environment is substantially changed in a selective manner with respect to one microorganism or more, but not equally for all microorganisms, e.g., by physical means or by metabolic amendment which is preferentially biodegraded and utilized by the preferred species.

By "physical means" is meant that the selective habitat enhancer does not function primarily by biodegradation of a provided agent but rather functions primarily, e.g., by selectively providing physical protection (shelter) or a suitable microclimate or microenvironment favorable to one or more of the desired species in the phylloplane such that the growth thereof is preferentially enhanced, e.g., over that of a species whose growth is to be controlled. The "shelter" can be from predation, from adverse effects of UV and/or IR radiation, from weather (e.g., wind, precipitation, aridity (by providing a local relatively high humidity)), etc. Other agents can also be included to augment this effect, such as agents which modify UV and IR effects, for example, IR reflectors, e.g., light colored or white materials, and UV absorbers, e.g., molecules containing carbon-carbon double bonds; agents which modify humidity effects, for example, humectants; buffers; etc. Thus these physical effects generally operate via the foliar coating provided by this invention which provides or enhances protection against weathering by means such as a fold, raised surface, indentation, crevice, etc., in the coating, or which filters out UV and/or IR wavelengths from radiation impinging on microorganisms entrapped within such loci, or which impedes evaporation of water or attracts the accumulation of water. Thus, generally, the term "habitat enhancer", as it refers to the physical effects provided, means a material or materials which selectively enhances the growth of a preferred species by providing a suitable physical environment favoring its growth and replication.

By "metabolic amendment" is meant that the selective habitat enhancer functions primarily by biodegradation of a provided agent as a selective food source for the preferred microorganism. Thus, for example, the polymeric substrate which is applied may be one which is subject to degradation primarily by means of enzymes which the preferred microorganism possesses, and thus represents a source of nutrients not available, or available only to a lesser extent, to the microorganism whose growth is to be controlled, and thereby the growth of the preferred microorganisms is enhanced over that of the microorganism whose growth is to be controlled. Thus, generally, the term "habitat enhancer", as it refers to the metabolic effects provided, means a material which is selectively degraded as a food source by and thereby enhances the growth of a preferred species by providing a suitable selective nutritional source favoring its growth and replication.

In either case, the enhancement of growth of the preferred species may result in one or more effects which substantially affect the microfloral composition of the foliar locus, especially with respect to the species whose growth is to be controlled. Non-limiting examples of these effects include the possibility that the durable selective habitat enhancer may function by enhancing the growth of the preferred microorganism, which in turn causes selective pressures well known to those of skill in the art; these selective pressures can result in the preferred species advantageously competing with other species for other limited nutrient resources, to the detriment of the other species. These limited nutrient sources at the foliar locus include, e.g., leaf exudates and leachates and deposited organic matter such as pollen and aphid honeydew. Another possibility is that the preferred species whose growth is enhanced produces an antibiotic that either inhibits the growth or replication of other organisms in the phylloplane, or that is lethal to them. For example, many bacteria and fungi produce antibiotics that are effective against plant pathogens. Still another possibility is direct parasitism of the pathogen by the preferred species, which is enabled to gain a foothold in the foliar environment by having a selective advantage as supplied by the habitat enhancer, either as food or shelter.

The preferred species may consist of a single species or multiple species They may co-exist in order to enhance each other's growth, or they may co-exist independently to antagonize one or more microbial plant pathogens. They may be endogenous to the foliar locus or applied simultaneously with the durable selective habitat enhancer, or sequentially, either prior to or after the application of the durable selective habitat enhancer.

The term "polymeric substrate" as used herein means materials composed of straight-chain and/or branched-chain polymers. These include, but are not limited to, polysaccharides, polypeptides, especially proteins, and polynucleotides. These may be natural biomolecules or synthetic polymers. They also include polymers which may or may not be metabolizable by a given microorganism. Thus, if the polymeric substrate is to function as a durable selective habitat enhancer primarily by physical means, as described above, it is preferred that the polymer be non-metabolizable. However, if the polymer functions primarily as a food amendment for the preferred species of microorganism, it is preferred that the polymer be metabolizable by the preferred species, preferentially to its metabolism by the species whose growth is to be controlled.

Excluded from the scope of polymeric substrates of this invention are commercial slow-release polymeric formulations wherein a desired ingredient is absorbed or adsorbed or covalently bonded to a polymer. In such prior art embodiments, the polymer per se is not biodegraded but merely serves as a source of the desired ingredient.

"Polymers" in this invention generally refer to materials having a degree of polymerization (number of polymerized monomer units) of at least 20, preferably 100-250 monomeric units, typically of a weight average molecular weight of about 4000-10,000 daltons. More particularly, in the case of polymers whose monomeric units are substantially soluble in water, polymers according to this invention include materials which are polymerized to the extent that they are substantially insoluble in water. The substrates may of course contain innocuous byproducts such as low molecular weight materials from the same monomers.

By "substantially insoluble" is meant a solubility in water at 20° C. of at most 10%, preferably <1%, most preferably essentially completely insoluble in water. Thus, the materials of this invention, when in the form to be applied to the plants, will be substantially in the form of a suspension or a sol, rather than a solution.

Suitable polysaccharide substrates include, but are not limited to, polysaccharides which can be biodegraded by some microorganisms. Non-limiting examples of the wide range of suitable polysaccharides include chitin, cellulose, β-1,3-glucans, carrageenan, poly(galacturonic acid) such as pectin, lignin and its derivatives, polylevulan, hemicellulose, xylan and mucopolysaccharides, and derivatives thereof, e.g., sulfated, nitrated, aminated, and phosphorylated derivatives. Nitrated and aminated derivatives are preferred.

It is preferred that the polymeric substrate of this invention, especially when it is a polysaccharide, be applied in a form that is conducive both to application protocols and/or to make the polymers enzymically available to the microorganisms as a habitat enhancer. This form may be achieved through the controlled hydrolysis of a complex, especially crystalline, polymer by an acid, a base or an enzyme to a less compact conformation. Thus, for example, in the case of chitin, hydrolysis of the highly crosslinked crystalline form of chitin to a long-chain branched form which is amorphous and fluffy in appearance is preferred. The hydrolysis should be of a limited extent such that the majority of the polymeric substrate remains substantially insoluble in water.

Chitin is a particularly preferred polymeric substrate. It is comprised primarily of poly(1→4)-N-acetyl-D-glucosamine, and is a polysaccharide found in nature in the cell walls of fungi, nematode egg shells, and insect and crustacean exoskeletons. It is preferred that the chitin used in this invention be hydrolyzed prior to application, to the extent necessary to break tertiary crystalline structure and thereby form amorphous material, e.g., by the use of an acid, base, or enzymatically, using conventional protocols, e.g., as described in the examples. Thus it is preferred that the chitin be hydrolyzed to the extent of, for example, having a weight average molecular weight of about 4000–10,000 daltons, as described above.

Cellulose, poly-β-(1→4)-glucose, is also a naturally occurring polysaccharide. Only a few organisms, including representatives of bacteria, actinomycetes and fungi contain cellulolytic enzymes.

Other suitable polymeric substrates include polypeptides and polynucleotides, as well as terpenes, long chain fats and oils and other like polymers, and combinations thereof.

Suitable physical sheltering polymers useful in this invention include any of the above-listed polymers which cannot be biodegraded by the relevant microorganism.

The term "binder" as used herein means a material which enhances the durability of the polymeric substrate upon the foliar locus. A suitable binder will thus adhere the agent to the desired surface and help prevent it from washing or weathering off the leaves. Suitable binders include, but are not limited to, drying oils and latex derivatives. Suitable drying oils include, for example, soybean oil, tung oil and linseed oil, as well as any conventional binder known in the art of herbicides and insecticides which are not toxic to the preferred microorganisms. Suitable binders of these types can be routinely determined by one of ordinary skill in the art. Other agents which may be useful as binders include polypectates and gums. Especially in the case of latexes being used as binders, there may be present other materials in the form of copolymers with the latex such as organosilicones, such as, for example, SILWET® (Union Carbide, Danbury, Conn.). It is further noted that, especially in the case when oils and/or fats are used as the binder, and especially when these oils or fats contain 16–24 carbons per molecule, the binder may simultaneously serve as both a binder and a substrate for the growth of the microorganism.

In addition to drying oils, the formulations of this invention may include other adjuvants which potentiate the adhesion of the durable selective habitat enhancer to the foliar locus or achieve other desirable effects such as surfactants, buffering agents, dispersants, wetting agents, etc. These materials are well known in the art, and their suitability for a particular application of this invention can be routinely determined, as above.

Other optional adjuvants which enhance the growth of the preferred organism are also contemplated. These can include, but are not limited to, humectants such as, for example, carboxymethyl cellulose, for increasing the moisture content of the polymeric substrate; IR-reflecting materials, for example, materials which impart a white, IR-reflective surface to the habitat enhancer, to prevent damage from solar radiation; UV-absorbing materials such as, for example UVnul® or lignin, also to prevent damage from solar radiation; surfactants, particularly organosilicone types, or others which are of low toxicity to microorganisms; and other adjuvants such as buffers, as mentioned above. These adjuvants can be added in amounts of 0.005 to 5.0% of the formulation, more or less also being useful.

In particular, the addition of UV-absorbing agents is well-known as a method of stabilizing UV-sensitive materials such as polymers, especially polymeric and oligomeric UV absorbers and especially those containing double-bonded carbon atoms. A low weight percentage of such agents (0.01 to 2.0% of the formulation, more or less also being useful) distributed uniformly throughout the material to be protected can provide dramatic and long-lasting reductions of levels of UV radiation within and/or underneath the material. Polymeric agents capable of performing in this fashion are reviewed extensively by D. Bailey and O. Vogl, J. Macromol. Sci. Rev. Macromol. Chem. C14(2), 267–293 (1976) and D.A. Tirrell, Polymer News 7:104–110 (1981). Examples of such UV-absorbing agents suitable for this invention include but are not limited to microbially non-toxic amounts of:

2-hydroxy-4-methacryloxybenzophenone/ethylene homopolymer;
2-hydroxy-4-methacryloxybenzophenone/vinylidene chloride homopolymer;
2-hydroxy-4-methacryloxybenzophenone/alkyl acrylate homopolymer;
2-hydroxy-4-acryloxybenzophenone/ethylene homopolymer;
2-hydroxy-4-acryloxybenzophenone/vinylidene chloride homopolymer;

2-hydroxy-4-acryloxybenzophenone/alkyl acrylate homopolymer;
2-hydroxy-4-methacryloxybenzophenone/ethylene copolymer;
2-hydroxy-4-methacryloxybenzophenone/vinylidene chloride copolymer;
2-hydroxy-4-methacryloxybenzophenone/alkyl acrylate copolymer;
2-hydroxy-4-acryloxybenzophenone/ethylene copolymer;
2-hydroxy-4-acryloxybenzophenone/vinylidene chloride copolymer;
2-hydroxy-4-acryloxybenzophenone/alkyl acrylate copolymer;
2-hydroxy-4-acryloxybenzophenone/styrene copolymer;
2-hydroxy-4-methacryloxyacetophenone/ethylene homopolymer;
2-hydroxy-4-methacryloxyacetophenone/vinylidene chloride homopolymer;
2-hydroxy-4-methacryloxyacetophenone/alkyl acrylate homopolymer;
2-hydroxy-4-acryloxyacetophenone/ethylene homopolymer;
2-hydroxy-4-acryloxyacetophenone/vinylidene chloride homopolymer;
2-hydroxy-4-acryloxyacetophenone/alkyl acrylate homopolymer;
2-hydroxy-4-methacryloxyacetophenone/ethylene copolymer;
2-hydroxy-4-methacryloxyacetophenone/vinylidene chloride copolymer;
2-hydroxy-4-methacryloxyacetophenone/alkyl acrylate copolymer;
2-hydroxy-4-acryloxyacetophenone/ethylene copolymer;
2-hydroxy-4-acryloxyacetophenone/vinylidene chloride copolymer;
2-hydroxy-4-acryloxyacetophenone/alkyl acrylate copolymer;
2-hydroxy-4-acryloxyaceto-phenone/styrene copolymer.

The durable habitat enhancers of this invention can also be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well known to those skilled in the art. Some are listed below:

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-(trichloromethylthio)tetrahydrophthalimide (captan)
N-(trichloromethylthio)phthalimide (folpet)
dimethyl 4,4'-(O-phenylene)bis(3-thioallophanate)(thiophanate-methyl)
2-(thiazol-4-yl)benzimidazole (thiabendazole)
aluminum tris (O-ethyl phosphonate)(phosethyl aluminum)
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[1,1,2,2-tetrachloroethyl)thio]cyclohex-4-ene-1,2-dicarbioximide (captafol)
3-(3,5-dichlorophenyl)-N-(1-methylethyl)-2,4-dioxo-1-imidazolidine carboxamide (iprodione)
3-(3,5-dichlorophenyl)-5-ethenyl-5-methyl-2,4-oxazolidinedione (vinclozolin)
kasugamycin
)-ethyl-S,S-diphenylphosphorodithioate(edifen-phos)
4-(3-(4-(1,1-dimethylethyl)phenyl)-2-methyl)-propyl-2,6-dimethylmorpholine (Fenpropimorph)
4-(3,4(1,1-dimethylethylphenyl)-2-methyl)propylpiperidine (Fenpropidine)
1-[[(bis(4-fluorophenyl)methylsilyl]methyl]-1H-1,2,4-triazole (flusilazole)
2-p-chlorophenyl-2-(1H-1,2,4-triazol-1-ylmethyl)-hexanenitrile (myolobutanil)
(±)-1-[2-(2,4-diohlorophenyl)-4-propyl-1,3-dioxolan-2ylmethyl]-1H-1,2,4-triazole (propiconazole)
N-propyl-N-[2-(2,4,6-trichlorophenoxy)ethyl-]imidazole-1-carboxamide (prochloraz)
(RS)-2,4'-difluoro-α-(1H-1,2,4-triazol-1-ylmethyl)-benzhydryl alcohol (flutriafol)
1-(4-chlorophenoxy)-3,3-dimethyl-1-(1H-1,2,4-triazol-1yl)butanone (triadimefon)
1-(4-chlorophenoxy)-3,3-dimethyl-1-(1H-1,2,4-triazol-1-yl)butan-2-ol (triadimenol)
(2RS,3RS)-1-(2,4-dichlorophenyl)-4,4-dimethyl-2-(1H-1,2,4-triazol-1-yl)pentan-3-ol (diclobutrazol)

Bactericides:
tribasic copper sulfate
streptomycin sulfate
oxytetracycline

Acaricides:
senecioic acid, ester with 2-sec-butyl-4,6-dinitrophenol (binapacryl)
6-methyl-1,3-dithiolo[2,3,B]quinonolin-2-one (oxythioquinox)
2,2,2-trichloro-1,1-bis(4-chlorophenyl)ethanol(dicofol)
bis(pentachloro-2,4-cyclopentadien-1-yl) (dienochlor)
tricyclohexyltin hydroxide (cyhexatin)
hexakis(2-methyl-2-phenylpropyl)distannoxane (fenbutin oxide)

Nematocides:
2-[diethoxyphosphinylimino]1,3-diethietane (fosthietan)
S-methyl 1-(dimethylcarbamoyl)-N-(methylcarbamoyloxy)-thioformimidate(oxamyl)
S-methyl 1-carbamoyl-N-(methylcarbamoyloxy)thioformimidate
N-isopropylphosphoramidic acid, O-ethyl O'-[4-(methylthio)-m-tolyl]diester (fenamiphos).

Insecticides:
3-hydroxy-N-methylcrotonamide(dimethylphosphate)ester (monocrotophos)
methylcarbamic acid, ester with 2,3-dihydro-2,2-dimethyl-7-benzofuanol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)

methyl N-[[(methylamino)carbonyl]oxy]ethanimidothioate (methomyl)

N'-(4-chloro-o-tolyl)-N,N-dimethylformamidine (chlordimeform)

O,O-diethyl-O-(2-isopropyl-4-methyl-6-pyrimidyl)-phosphorothioate (diazinon)

octachlorocamphene (toxaphene)

O-ethyl O-p-nitrophenyl phenylphosphonothioate (EPN)

cyano(3-phenoxyphenyl)-methyl-4-chloro-α-(1-methylethyl)benzeneacetate (fenvalerate)

(3-phenoxyphenyl)methyl(±)-cis,trans-3-(2,2-dichloroethenyl)-2,2,-dimethylcyclopropanecarboxylate (permethrin)

dimethyl N,N'-[thiobis(N-methylimino)carbonyloxy]]-bis[ethanimidothioate](thiodicarb)

phosphorothiolothionic acid, O-ethyl-O-[4-(methylthio)phenyl]-S-n-propyl ester (sulprofos)

α-cyano-3-phenoxybenzyl 3-(2,2-dichlorovinyl)-2,2-dimethylcyclopropane carboxylate (cypermethrin)

cyano(3-phenoxyphenyl)methyl 4-(difluoromethoxy)-α-(methylethyl)benzeneacetate (flucythrinate)

O,O-diethyl-O-(3,5,6-trichloro-2-pyridyl)phosphorothioate (chlorpyrifos)

O,O-dimethyl-S-[[(4-oxo-1,2,3-benzotriazin-3-(4H)-yl)methyl]phosphorodithioate (azinphos-methyl)

5,6-dimethyl-2-dimethylamino-4-pyrimidinyl dimethyl carbamate (pirimicarb)

S-(N-formyl-N-methylcarbamoylmethyl)-O,O-dimethylphosphorodithioate (formothion)

S-2-(ethylthioethyl)-O,O-dimethyl phosphiorothioate (demeton-S-methyl)

α-cyano-3-phenoxybenzyl cis-3-(2,2-dibromovinyl)-2,2-dimethylcyclopropane carboxylate (deltamethrin)

cyano(3-phenoxyphenyl)methyl ester of N-(2-chloro-4trifluoromethylphenyl)alanine (fluvalinate).

The durable selective habitat enhancers of this invention can be applied by fully conventional techniques known for applying formulations, e.g., liquids to foliage.

Possible formulation types include dusts, granules, pellets, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and optionally (a) about 0.1% to 2% surfactant(s) and (b) about 1% to 99.9% solid or liquid inert diluent(s). More specifically, they will contain these ingredients in the following approximate proportions:

| | Active Ingredient | Weight Percent* | |
|---|---|---|---|
| | | Diluent(s) | Surfactant(s) |
| Wettable powders and water dispersible granules | 20-90 | 0-74 | 1-10 |
| Oil suspensions, emulsions, (including emulsifiable concentrates) | 3-50 | 40-95 | 0-15 |
| Aqueous suspension concentrates | 10-50 | 40-84 | 1-20 |
| Dusts | 1-25 | 70-99 | 0-5 |
| Granules and pellets | 0.1-95 | 5-99.9 | 0-15 |
| High strength compositions | 90-99 | 0-10 | 0-2 |

*Active ingredient plus optionally one of a surfactant or a diluent equals 100 weight percent.

Lower or higher levels of active ingredient can, of course, be present depending on the intended use and the physical properties of the ingredients. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions, e.g., intermediate compositions, are prepared by simply mixing the ingredients. Fine solid compositions are made, e.g., by blending and, usually, grinding as in a hammer or fluid energy mill. Water dispersible granules may be produced, e.g., by agglomerating a fine powder composition (see, for example, B. Cross and H. Scher, "Pesticide Formulations", ACS Symposium Series 371, American Chemical Society, Washington, D.C., 1988, pp. 251-159). Suspensions are prepared, e.g., by wet milling (see, for example, Littler, U.S. Pat. No. 3,060,084). Granules and pellets may be made, e.g., by spraying the active material upon preformed granular carriers or by agglomeration techniques. See J.E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H.M. Loux, U.S. Pat. No. 3,235,361, Feb. 15, 1966, Col. 6, line 16 through Col. 7, line 19 and Examples 10 through 41;

R.W. Luckenbaugh, U.S. Pat. No. 3,309,192 March 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, Jun. 23, 1959, Col. 3, line 66 through Col. 5, line 17 and Examples 1-4;

G.C. Klingman, "Weed Control as a Science", John Wiley and Sons, Inc., New York, 1961, pp. 81-96; and J.D. Pryer and S.A. Evans, "Weed Control Handbook", 5th Ed., Blackwell Scientific Publications, Oxford, 1968, pp. 101-103.

Suitable amounts of the durable selective habitat enhancer can be routinely determined, and application of these amounts can be achieved, for example, by spraying the plants until the point of runoff of the solution. Other methods of application will also be suitable, depending upon the technique chosen.

The timing for applications can be routinely determined and adapted for a particular plant, pathogen and antagonist by one of ordinary skill in the art. Thus it may be preferable for a particular plant to be treated prophylactically when there is a known threat of a particular pathogen, or it may be preferable to wait until there are early signs of infection. It may be preferable to apply the durable selective habitat enhancer at a particular point in a particular plant's life cycle; for example, at leaf budding, abscission or setting of fruit. In other cases, application may be timed by the weather or time of year, which favors the growth of certain plant pathogens. Still further, applications may be single or multiple, depending upon the durability of the durable selective habitat enhancer and, if it is a biodegradable food source, for example, for the preferred species, the rate at which it is being used up. Other factors in determining the frequency of reapplication include the growth rate of new foliage on the plants, the rate of environmental erosion, the frequency of infection events, the frequency of insect flights, etc. These factors are routine, and application intervals can be determined analogously to standard methods used in the agricultural industry.

The durable selective habitat enhancer of this invention is preferably applied, e.g., in colloidal suspensions in concentrations of, for example 0.1 to 5.0%, w/w of water. These suspensions can generally contain, for example, from 0.2 to 1.0% of the habitat enhancer (for example, preferably about 0.5 for chitin and 1.0% for cellulose), 0.001 to 0.02% of the binder, and 0.001 to 0.1% of the other adjuvants.

If desired, the durable selective habitat enhancer can be produced and stored in concentrate form of 2 to 25%, w/w, suspended in water, and can be diluted with water to the appropriate concentration for application just prior to use. Alternatively, the enhancer can be prepared in wettable powder form or dispersable granule form and made up with water at the time of application.

It will be appreciated that the concentration of the inoculum of microorganism which can optionally be applied exogenously to the plants before, during or after treatment with the durable selective habitat enhancer will vary depending upon the type of microorganism, the field conditions, how it is applied, etc. Suitable concentrations can be routinely determined by one of skill in the art. Suitable culturing conditions for growing the large quantities needed of any particular microorganism are similarly highly conventional, including suitable nutrient media, liquid and solid substrate fermentation equipment, temperatures, methods of determining cell concentrations, etc. The microorganisms may be applied as a metabolically active form or in spore form. The microorganisms preferably will be added to the durable selective habitat enhancer just prior to application to the plants, if they are coapplied. Otherwise, they can be applied to the plants, e.g., as a spray at the appropriate concentrations suspended in, e.g., a binder, either before or after application of the habitat enhancer of this invention. If the microorganisms are applied prior to the application of the habitat enhancer, however, it is preferred that they be applied only shortly before the habitat enhancer is applied, in order for the full benefit of the protective and/or nutrient selectivity of the habitat enhancer to be obtained. It is also possible that the microorganism can be present in the suspensions, concentrates or powders containing the habitat enhancers of this invention which can be stored, if the suspensions or concentrates are frozen, or at room temperature if the microorganism is present in an inactive form, such as in the form of spores contained in the powders.

A preferred formulation of, for example, chitin and a drying oil into a colloidal suspension for foliar application as a durable selective habitat enhancer according to this invention resulted in durable persistent residues capable of modifying the population of extant epiphytic microorganisms and also enhancing the survivability of applied chitinolytic bacteria. The ability to manipulate populations of epiphytic microorganisms by the application of, for example, chitin indicated a potential for biocontrol. A model pathogen/host system, *Cercospora arachidicola* on peanut, was studied, with and without the application of an exogenous microorganism. The exogenously applied microorganisms chosen for this system was a *Bacillus cereus* strain originally isolated from field-grown peanuts treated with the colloidal chitin formulation and selected as a potential antagonist because of its chitinolytic activity, as well as its ability to colonize field-grown peanut leaves. *Curtobacterium flaccumfaciens* was isolated from greenhouse-grown peanuts and selected as a potential antagonist because it was a prolific chitinase producer.

The use of an inexpensive, industrial grade chitin (Clandosan ®) resulted in more dramatic shifts in populations of epiphytic microflora than purified chitin (P-chitin). The incorporation of a calcium carbonate buffer into the formulation further accentuated shifts in microbial populations and enhanced the survival of the two exogenously applied bacterial antagonists. A 60% reduction in disease severity compared to untreated controls occurred on plants treated with buffered Clandosan ® +*B. cereus*, which exhibited better survivability and disease suppression overall than *C. flaccumfaciens*. *B. cereus* was reisolated from inoculated, Clandosan ®-treated plots at populations of $3\times10^4$ cell/gram of leaf tissue 7 days after application. Viewing the leaf surface with an electron microscope, Bacillus cells could be seen dividing and growing.

Another preferred formulation comprising cellulose +Soydex ® (85% soybean oil:15% surfactant; Helena Chemical Co., Memphis, TN) similarly exhibited good durability and weatherability on foliar surfaces. Applying amorphous cellulose to the leaves created physical environments which improved survival of microbial antagonists, e.g., by protecting them from UV and IR irradiation and desiccation. These polymers can also form a physical barrier which prevents infection by foliar pathogens. Another approach involved the application of the cellulolytic fungal antagonist *Chaetomium globosum* as a means of biological control of pathogens, which was compared with and without the addition of a durable selective habitat enhancer according to this invention. The severity of apple diseases flyspeck (*Zygophiala jamaicensis*) and sooty blotch (*Gloeodes pomigena*) were significantly reduced by the treatments according to the invention. Cellulose +*C. globosum* reduced the number of flyspeck infection loci by 63% while cellulose alone reduced the number by 36% over the untreated control. Chaetomium survival and growth were increased significantly by the addition of cellulose (which probably functioned as a source of food), but not by the addition of chitin; indigenous phylloplane populations were suppressed by *C. globosum* growth.

Disease suppression can result from the lysis of fungal cell walls by the chitinase-producing antagonists and by enriched populations of native chitinolytic microorganisms. Scanning electron microscopy showed that the applied bacteria colonized and digested chitin particles and fungal hyphae. The nature of the chitin formulation on the leaf surface provides potential physical environments suitable for colonization by microorganisms, and forms a physical barrier that may prevent the germination of spores of pathogenic microorganisms landing on it. Direct antibiosis through the production of inhibitory compounds by the applied bacteria can also occur.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

Example 1: Addition of Metabolic Amendment a. Effect on resident foliar microorganisms
b. Effect on applied microorganism

Methods

A colloidal suspension of chitin was prepared by acid hydrolysis of 3 kg of flaked crustacean chitin (Sigma Chemical Co.) in 23 L of concentrated HCl. Rodriguez-Kabana et al. (1983). The mixture was allowed to stand for 2 hours at 28° C. until dissolved, then diluted with 114 L of water, stirred, and allowed to settle overnight. The supernatant was siphoned off and discarded. Fresh water was added, and the suspension was mixed thoroughly and allowed to resettle. The rinsing process was repeated twice daily for 7–10 days until the pH exceeded 2.0. The concentrated chitin suspension was then filtered through a 0.7 mm mesh screen, placed in 1 gal containers, and stored at 4° C. The chitin concentration of the final suspension was determined by drying 1 ml samples in a tared watch glass at 60° C. for 10 h. Dry weight was determined to the fifth decimal place.

Preliminary Test and Bacterial Culture

A 1% solution of colloidal chitin was applied until just before runoff to 5-wk-old, field-grown peanuts, in a non-replicated test to evaluate several spray adjuvants, e.g., stickers and spreaders, for the desired coverage and weathering characteristics. Visual monitoring of the deposits and an evaluation regarding the ease with which the deposits could be rubbed off were performed. After 2 weeks, samples of the phylloplane microflora were collected using leaf wash and dilution plate techniques, and cultures were grown on nutrient agar containing 0.2% chitin. A chitinolytic, spore-forming *Bacillus cereus* Cohn was selected from these cultures and transferred to nutrient broth containing 0.4% chitin. Broth cultures were placed on a rotary shaker for 5 days, after which they were harvested by filtration through a Whatman No. 2 filter. Cells were rinsed from the filter with sterile water, and the turbidity of the solution was optically adjusted to 1.0–5.0$\times 10^8$ cells/ml.

Field Trials

Concentrations of chitin, *B. cereus*, and a fungicide control (commercial standard) were tested for effects on epiphytic microbial populations under field conditions at the Auburn University Agronomy Farm, Auburn, Alabama. "Florunner" peanuts were planted in rows 0.8 m apart. The aqueous concentrations of chitin tested were 0.0%, 0.1%, 0.2%, 0.5%, and 1.0%. Control plots were treated with chlorothalonil (500 gl/L flowable, Bravo 500L®, Fermenta Plant Protection, Painesville, Ohio) at 2.3 L/ha. A soybean oil-surfactant blend (SOSB) (85%:15% soybean oil:surfactant, Soydex® Helena Chemical Co., Memphis, Tennessee) was added as an adjuvant to all treatments at 0.25%. The chitin and fungicide treatments were applied with or without *B. cereus* beginning 56 days after planting. The 12 treatments were arranged as single row plots 1.5 m long in a randomized complete block design, each with three replications. All treatments were applied until just before runoff (approximately 650 L/ha). One hundred ml of the concentrated bacterial cell suspension wa added to 900 ml of water and applied to field plots subsequent to the application of the organic amendment. Applications were made with hand-held spray pump sprayers on a seven-day schedule beginning Jul. 20, 1986, and continuing for nine weeks (Sep. 25).

Sampling and Isolation of Organisms

Epiphytic populations were estimated by randomly collecting 10 g of leaf tissue from upper, middle, and lower portions of the peanut canopy beginning two weeks after the first treatment and continuing at four-week intervals throughout the season. The leaf samples were added to 100 ml of sterile tap water in 250 ml Erlenmeyer flasks. One drop of surfactant (Tween 20) was added as a wetting agent, and the flasks were placed on a rotary shaker at 100 rpm for 1 hour. The leaf wash solution was diluted by adding 1 ml of wash solution to a tube containing 9 ml of sterilized tap water. A second ten-fold dilution was made, and 0.1 ml of each dilution was transferred aseptically to 90 mm Petri plates containing 20 ml of the following medium: nutrient agar +0.2% chitin (CNA) to estimate actinomycete and bacterial populations, as well as their chitinolytic activity. Three replicate plates of CNA per plot were inoculated with leaf washates at dilutions of $10^{-3}$ g leaf tissue/ml water and $10^{-4}$ g leaf tissue/ml water. All plates were incubated at 30° C. for 5 days. Plate counts were expressed as colony-forming units/g wet leaf tissue (CFU/g). Colonies were counted using a dark field colony counter, and each was assumed to have developed from a single propagule. Fungi and dominant bacteria were identified to genus, and mean colony counts of the three replicate plates for each medium were determined.

Statistical Analysis

Statistical analyses were performed using microcomputer SAS general linear models procedures (SAS User's Guide, 1985). Treatment means were evaluated for least significant differences utilizing a Student T test. Unless otherwise stated, significant differences were at the 0.05 level of probability.

Results

Preliminary Test and Culture

The preliminary test indicated that the colloidal chitin suspension containing the soybean oil-surfactant blend (SOSB) exhibited excellent tenacity, remaining on the leaf surface for several weeks while withstanding heavy rain, wind, and intense solar radiation. *Bacillus cereus* was selected for use in subsequent tests from numerous chitinolytic bacteria isolated from the preliminary test plants and later was identified by fatty acid analysis (Microbial ID, Inc., Newark, Del.). This bacterium exhibited rapid growth in culture, as well as moderate chitinase production, and inhibition of adjacent colonies of some bacteria and fungi.

Field Test

Populations of epiphytic actinomycetes, bacteria, fungi, and yeasts were affected differently by application of chitin and/or the presence or absence of the applied chitinolytic bacteria *B. cereus.* Both qualitative and quantitative differences in organisms isolated on CNA from chitin-treated and untreated leaves were found. Midseason samples collected in early September at 100 days after planting showed a dramatic and highly significant increase in actinomycete populations with the addition of chitin (FIG. 1). Populations did not vary significantly in 0.2–1.0% chitin treatments in the absence of *B. cereus.* However, the addition of *B. cereus* resulted in a significant increase in actinomycete populations, with the highest numbers occurring with the addition of 0.2% chitin. The addition of *B. cereus* to the formulation control had no effect on actinomycete levels.

The late season isolation at 130 days after planting indicated a general decline in actinomycete numbers on plants treated with higher concentrations of chitin, as compared to those on plants treated with the formulation control and 0.1% chitin. The addition of *B. cereus* increased actinomycete numbers significantly in the presence of 1.0% chitin but decreased them significantly when added to the formulation control.

Neither the application of chitin nor the chitinolytic *B. cereus* bacterium caused any significant changes in populations of epiphytic bacteria at midseason. However, there was a general trend ($P<0.10$) for *B. cereus* to cause a decline in the numbers of epiphytic bacteria. Late in the season, the rate of chitin caused a highly significant ($P<0.01$) increase in total epiphytic bacteria populations. In the presence of chitin, the addition of *B. cereus* caused a further increase in populations of epiphytic bacteria (disregarding the applied *B. cereus*).

The incidence of early leafspot, caused by *C. arachidicola*, was determined by an objective rating system (data not presented). Disease severity on fungicide-treated peanuts was lower than those treated with the chitin formulation or controls. Disease severity was not significantly different among chitin treatments, indicating that this portion of the leaf microflora was not affected by the formulations tested.

Discussion

The addition of SOSB to the colloidal chitin suspension provided it with extended weatherability such that the spray interval of 7–10 days was a function of the need to treat new foliage rather than the loss of residue, which remained visible for periods of greater than one month. The extended period of time that the chitin suspension remained on the leaf facilitated the development of a greatly increased microflora (0.5–1.0 $\log_{10}$) in general, and also of a large population of chitinolytic microflora, indicating the bio-availability of the colloidal chitin. *Bacillus cereus* was selected from this modified microflora as a suitable organism to apply to leaf surfaces in subsequent tests for several reasons: (1) *B. cereus* is a Gram-positive, spore-forming bacterium, providing it with environmental insensitivity: (2) cultures on chitin agar showed it to be a rapid-growing, chitinase producer that occurred in moderate numbers on peanut leaves, and (3) Bacillus spp. are known to produce a variety of antibiotics which was illustrated by the inhibition of some bacteria and numerous fungi by *B. cereus* in culture, suggesting that this may also occur on the leaf surface (data not presented).

For bacterial antagonists applied to foliage, the major cause of cell death is desiccation (Leban et al., 1965). Moisture is also one of the major limiting factors in the growth and reproduction of the naturally occurring epiphytes. The unusually hot and dry conditions during the summer of 1986 probably caused the total populations of epiphytic organisms to be lower than during a cooler, wetter year. However, the data indicated overall increases in the populations of epiphytic actinomycetes, bacteria, and fungi with the addition of chitin. Microbial isolations indicated that the added *B. cereus* was surviving at populations of up to $1\times10^4$ CFU's/g wet leaf tissue seven days after being applied to field plots.

Bacteria and actinomycetes have been reported to be the predominant colonizers of leaf tissue early in the growing season, while fungi and yeasts become dominant later in the season (Blakeman, 1985). The results presented here support these general patterns of succession. They were significantly influenced, however, by the addition of *B. cereus* and colloidal chitin, alone or in combination. Actinomycetes, which are considered to be the predominant microorganisms involved in chitin degradation and chitinase production in soil (Veldkamp, 1955) and which are stimulated by the addition of chitin to soil (Goday et al., 1983), also were stimulated by the addition of chitin and *B. cereus* to the leaf at midseason (FIG. 1). This increase was probably due to ability to degrade chitin through the production of chitinolytic enzymes. The tendency for populations of epiphytic bacteria to decline in the presence of *B. cereus* and chitin at midseason could be due to several factors. These include the bacterium having a competitive advantage for chitin as a food source and/or the production of antibiotics or other inhibitory compounds.

Overall results of population studies indicated that epiphytic microorganisms are affected differentially by the addition of large numbers of one component of the population in combination with a selective food source.

Example 2: Control of Foliar Pathogens by Addition of Metabolic Amendments

Introduction

*Cercospora arachidicola*, the causal fungus of early leafspot of peanut, is a destructive pathogen capable of causing up to 50% pod yield loss when not controlled with fungicide sprays (Smith, 1984). Management practices can aid in the reduction of initial inoculum, but primary control of early leafspot is through application of chemical fungicides such as chlorothalonil throughout the growing season.

Methods

Greenhouse Test and Bacterial Culture

A test was conducted in the greenhouse to select a formulation buffer of an appropriate pH for bacterial growth and enzymatic activity, but that was not phytotoxic. Four buffers (potassium phosphate pH 5.4, sodium propionate pH 6.4, calcium hydroxide pH 11.5, and calcium carbonate pH 8.0) were tested on greenhouse grown peanuts (data not presented). Two chitinolytic bacteria, *Bacillus cereus* Cohn isolated from field grown peanuts in 1986, and *Curtobacterium flaccumfaciens* (Hedges) Collins & Jones, isolated from greenhouse grown peanuts treated with buffered colloidal chitin and SOSB, were identified using fatty acid analysis (Microbial ID, Inc., Newark, Del.), and cultured in 2.8 liter Fernbach flasks containing 1 L of nutrient broth +0.4% chitin. Cultures were placed on a rotary shaker for 5 days and harvested by centrifugation at 5000 g for 10 minutes.

Field Trials

Two field tests were conducted at the Auburn University Agronomy Farm, Auburn, Ala. "Florunner" peanuts were planted May 5, 1987, using 0.8 m row spacing. In test a, two chitin preparations were compared. The first preparation utilized purified chitin (P-chitin) and was made using flaked crustacean chitin (Sigma Chemical Co.). P-chitin was used in the 1986 field trial and prepared as described in Example 1. The second chitin preparation, industrial chitin (Clandosan), was prepared from a ground chitin-protein complex (McCandliss et al., 1985), as described above. A 3×2 factorial design consisting of three levels of chitin which were: (1) a 1% suspension of P-chitin, (2) a 1% suspension of Clandosan, and (3) no chitin (control). Each level of chitin was applied in two forms: (1) buffered with a 1.0% suspension of $CaCO_3$ at pH 8.0 and (2) unbuffered. SOSB was added at 0.25% as a spray adjuvant to all treatments with the exception of the unbuffered, no chitin control. The six treatments were arranged using single row plots (2.5 m) in randomized complete blocks with six replications.

In test b, two chitinolytic bacteria were used in conjunction with Clandosan which was diluted to 1.0% w/v chitin and buffered using a suspension of $CaCO_3$ (1 gram/100 ml water) to pH 8.0. A soybean oil-surfactant blend (88:15, Soydex, Helena Chemical Co., Memphis, Tenn.) was added at 0.25% as a spray adjuvant. The chitin preparation was compared to untreated plots as well as to a formulation control consisting of $CaCO_3$+0.25% SOSB using a 3×3 factorial design. The three formulations included (1) Clandosan, (2) formulation control, and (3) untreated control. The three levels of applied organism were (1) no added organism, (2) *B. cereus*, and (3) *C. flaccumfaciens*. An aqueous suspension of approximately $10^8$ bacterial cells/ml +0.25% soybean oil-surfactant blend (SOSB) was applied to field plots. The nine treatments were arranged using single-row plots (3 m long) in randomized complete blocks with six replication per treatment.

Treatments were applied to peanuts in both tests using hand-held compressed air sprayers until just before leaf runoff (approximately 650 L/ha). A seven-day spray schedule was followed beginning June 19 and continuing through Aug. 29, 1987.

Disease Evaluations

Evaluations of early leafspot were made on both field tests concurrently using two methods. A subjective rating in which 1.0=no disease and 2.0=20% or more of total leaf area diseased was performed at crop maturity (85 days after planting). An objective rating (total lesions) was performed in which all early leafspot lesions occurring on leaflets at nodes 4, 7, and 10 from the shoot apex were counted.

Statistical Analysis

Statistical analyses were performed using microcomputer SAS (SAS User's Guide, 1985), general linear models and orthogonal comparison procedures. Unless otherwise stated, differences were significant at the 0.05 level of probability.

Results

Test a: Formulation Experiment

Greenhouse experiments to examine the performance of several buffers indicated that a suspension of calcium carbonate at pH 8.0 was not phytotoxic to peanut foliages, and was within an acceptable pH range for bacterial growth and enzyme production and activity (Rodriguez-Kabana et al., 1983). Excellent coverage and tenacity were exhibited by the formulation when calcium carbonate and SOSB were added to the colloidal suspensions of P-chitin and Clandosan. Scanning electron micrographs of untreated peanut leaves, and leaves treated with buffered colloidal Clandosan formulation illustrated an altered leaf surface topography with the addition of the chitin formulation.

Figure 2:
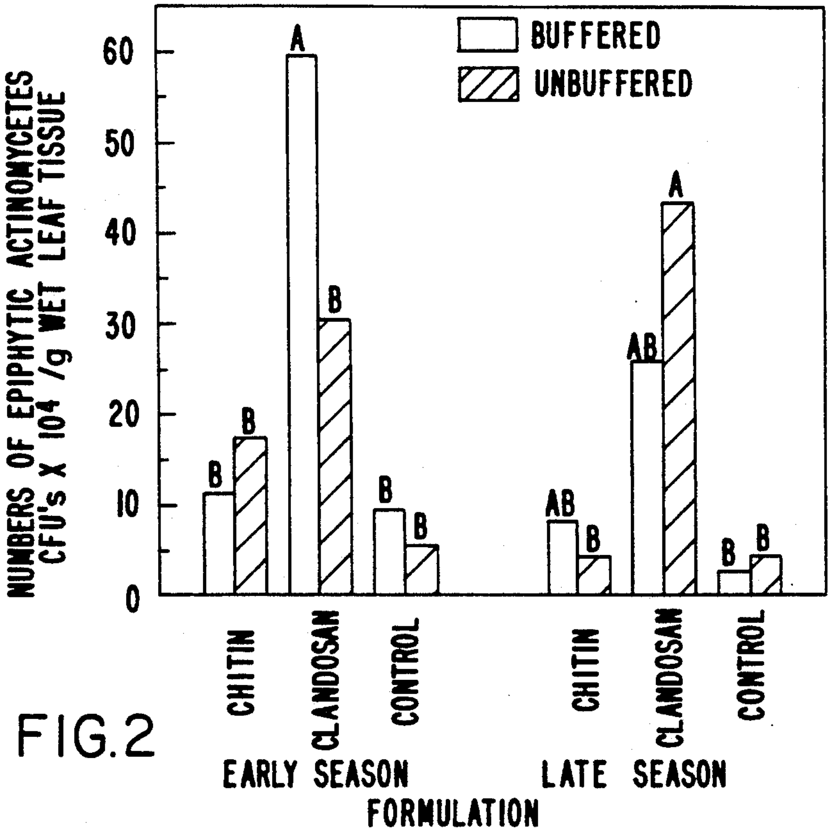
FIG. 2 shows the effect of buffer ($CaCO_3^-$), Clandosan and chitin on populations of actinomycetes on peanut leaves.
Figure 3:
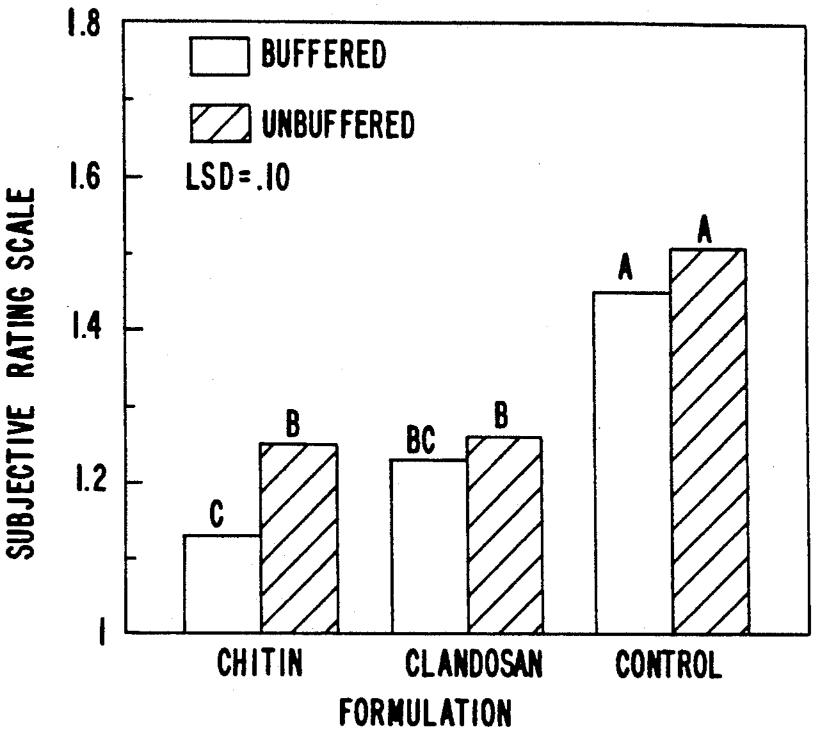
FIG. 3 shows the effect of buffered and unbuffered chitin formulations on peanut early leafspot disease severity using a subject rating scale where 1.0=no disease and 2.0=20% of leaves infected by *Cercospora arachidicola*.

Microbial isolations at 70 days (early) and 95 days (late) after planting indicated that numbers of epiphytic actinomycetes (FIG. 2) were highest on Clandosan treatments at both dates, with significantly higher levels in the buffered treatments early in the season. Orthogonal comparisons indicated increased populations of actinomycetes ($P=0.01$) on Clandosan treated plants compared to either P-chitin or control treatments. Buffered P-chitin was superior to the unbuffered formulation, indicating that buffering has some impact on reducing disease severity. This is supported by orthogonal analysis of unbuffered chitin treatments compared to buffered chitin treatments which indicated a reduction in disease severity ($P<0.04$) with buffering using the subjective disease rating system (FIG. 3).

Test b: Addition of Antagonists

Figure 4:
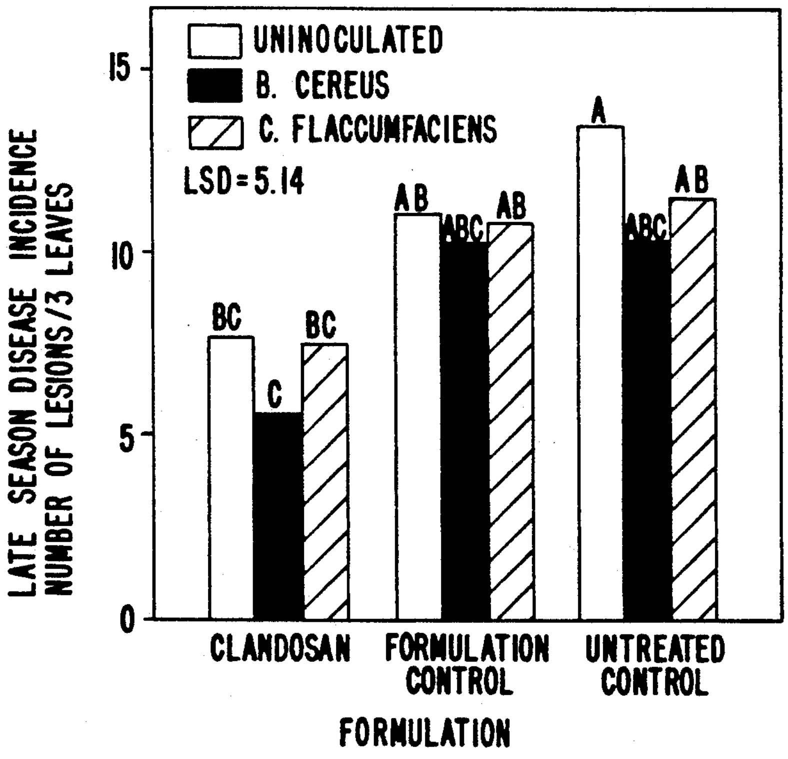
FIG. 4 shows the effects of two bacteria (*Bacillus cereus* or *Curtobacterium flaccumfaciens*) applied alone (with Soy-dex, a drying oil/sticker), with Soy-dex and buffers (formulation controls) or with Soy-dex, buffers, and Clandosan, on peanut leafspot disease severity.

Differences between treatments were apparent when the total lesion numbers of three leaves were used (FIG. 4). A 60% reduction in disease severity was recorded between untreated control plants and plants treated with Clandosan and *B. cereus*. Orthogonal comparison of all Clandosan-containing treatments to all formulation control treatments showed a highly significant ($P<0.01$) decrease in disease severity with the addition of Clandosan. Using orthogonal analysis, a highly significant ($P<0.01$) decrease in late season defoliation was evident when Clandosan treatments were compared to formulation treatments, and uninoculated Clandosan was compared to Clandosan +*B. cereus* or Clandosan +*C. claccumfaciens.*

Discussion

The objective rating system (number of lesions/3 leaves) was used to quantify differences between treatments. This system indicated that untreated control plants had four times as many lesions as plants treated with buffered Clandosan. Further, the buffered control treatment suppressed disease as well as the unbuffered chitin treatments indicating that the buffer and adjuvant mixture contributed to the effects of chitin in suppressing disease. This effect could be due to a more suitable pH for the growth of antagonists such as actinomycetes and fungi, which increased on buffered Clandosan. Reduced disease severity in the formulation control treatment could also be due to the SOSB acting as a metabolic amendment or possibly the toxic effect of the surfactants on the pathogen (Backman et al., unpublished result).

In Test b, the subject rating system indicated that the addition of *B. cereus* to untreated plants provided the same level of disease suppression as the chitin treatments, suggesting that *B. cereus* acted antagonistically to the pathogen. Both *B. cereus* and *C. flaccumfaciens*, as well as the formulation control, suppressed disease in the absence of chitin when percent infection was calculated. (The total lesion rating was more effective in elucidating differences between treatments.) The Clandosan formulation +*B. cereus* was the most effective treatment in suppressing disease, with a 60% reduction in the number of lesions compared to the untreated control. Using this evaluation system, a general trend for the addition of organisms to lessen lesion numbers became apparent. The numbers of added organisms were low when compared to total epiphytic bacteria, indicating that disease suppression on plots treated with bacteria was accomplished by a subdominant component of the microflora, i.e., approximately 2.4% of the total microflora 1 week after application. In the case of *B. cereus*, this response was significantly enhanced with the addition of chitin as were population levels of *B. cereus* at seven days following treatment, indicating that the organism was utilizing the amendment in some way.

Example 3: Electron Micrographic Studies of the Effects of Added Chitin and Added Microorganisms at the Foliar Locus

Methods

Leaves sampled from the experiment described in Example 1 were collected randomly, as were leaves from Example 2.

Electron Microscopy

Peanut leaf samples from all treatments were fixed for scanning electron microscopy (SEM) in formalin-acetic acid-alcohol fixative (FAA 5%, 5%, 70%) for 24 hours in a vacuum desiccator. Specimens were then dehydrated in a graded series of ethanol (50%-100%), critical point dried, mounted on aluminum stubs, sputter-coated with gold/palladium, and examined using an ISI Model SS40 scanning electron microscope at 5 kv.

Isolation of Organisms

Epiphytic populations were estimated by systematically collecting 10 g of leaf at 70 and 95 days after planting and were dilution plated to selective media as described in Example 1. The medium used was nutrient agar +0.2% chitin (CNA) to estimate populations of bacteria, including added bacteria, as well as chitinolytic activity. Three replicate plates per plot of CNA inoculated with dilutions of $10^{-3}$ g leaf tissue/ml water and $10^{-4}$ g leaf tissue/ml water. All plates were incubated at 30° C. for 5 days. Plate counts were expressed as colony-forming units/g wet leaf tissue (CFU/g).

Results

Leaf Ecology

Figure 5:
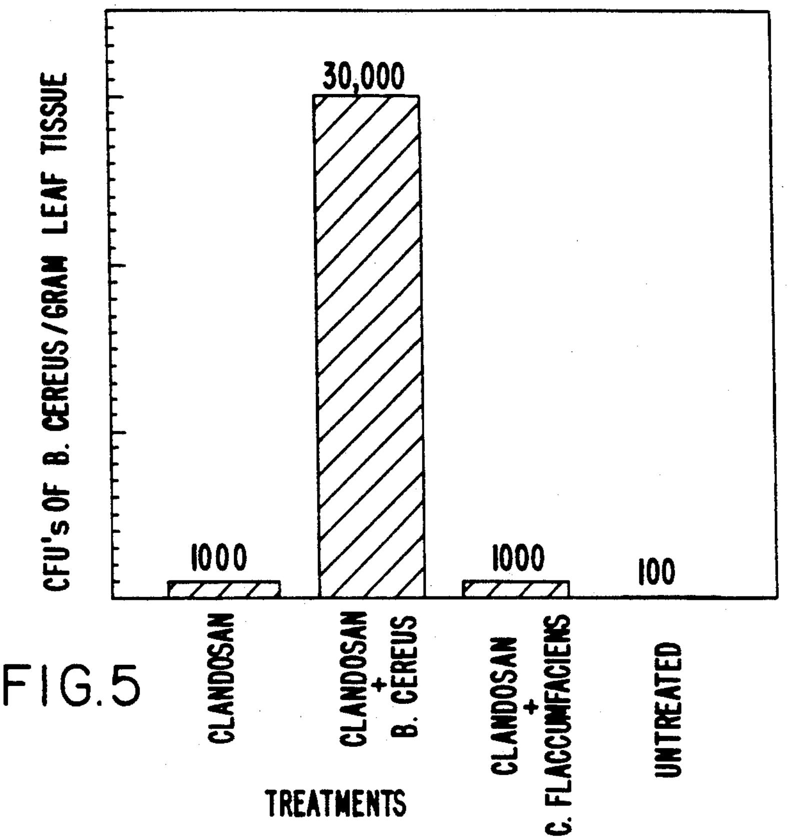
FIG. 5 shows the numbers of *Bacillus cereus* cells isolated from field grown peanut leaves 1 wk after application at $10^8$ cells/ml.
Figure 6:
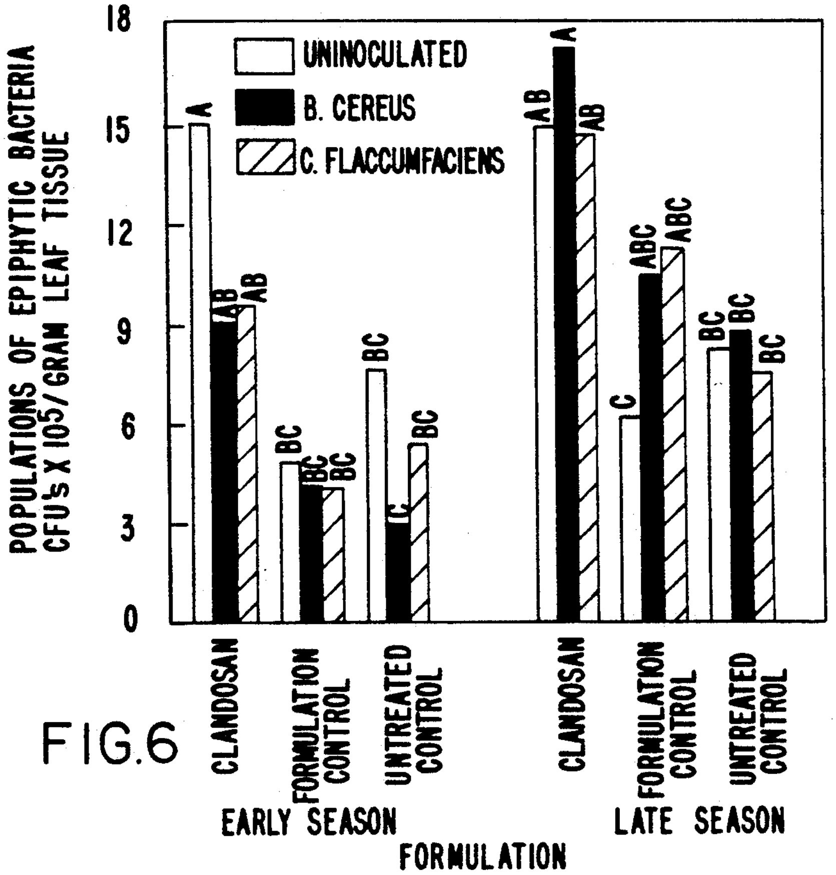
FIG. 6 shows the effects of formulation and applied bacteria on populations of epiphytic bacteria at early season (70 days) and late season (90 days). Treatments with the same letter are not significantly different ($P=0.05$)

Microbial isolation, as well as observation by scanning electron microscopy, indicated that both species of applied bacteria (*B. cereus* and *C. flaccumfaciens*) were surviving the application process and were reproducing on chitin-treated leaves at least seven days after application. FIG. 5 indicates that background populations of *B. cereus* on untreated plots were approximately 100 CFU's/gram leaf tissue. One week after application to chitin-treated leaves, *B. cereus* was isolated at $3\times10^4$ CFU's/gram leaf tissue. *Curtobacterium flaccumfaciens* was recovered from inoculated I-chitin (I-chitin=industrial chitin=Clandosan) treated plots at populations of $1\times10^2$ CFU's/gram leaf tissue five days after application (data not presented). Numbers of naturally occurring epiphytic bacteria (excluding added bacteria) on each of the nine treatments at early and late season isolations are represented in FIG. 6. At both sampling dates, chitin greatly increased (two- to three-fold) numbers of total epiphytic bacteria, while there was a general trend for the addition of either *B. cereus* or *C. flaccumfaciens* to reduce numbers of naturally occurring epiphytic bacteria, particularly at the early date. Orthogonal analysis indicated that there was a significant increase ($P<0.01$) in actinomycete populations in Clandosan treatments compared to formulation control treatments.

Figure 7:
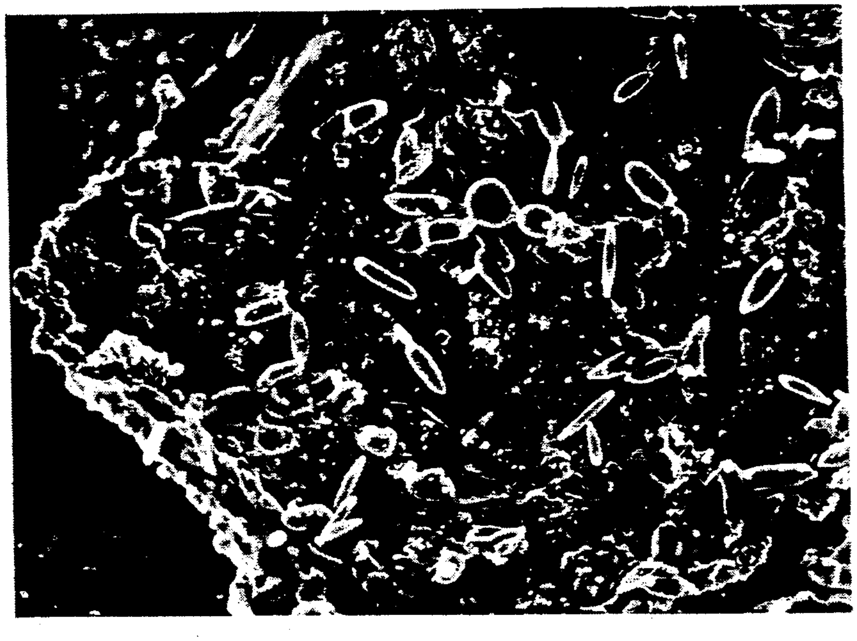
FIG. 7 shows a scanning electron micrograph of *Curtobacterium flaccumfaciens* and other naturally occurring microorganisms colonizing chitin 5 days after application.
Figure 8:
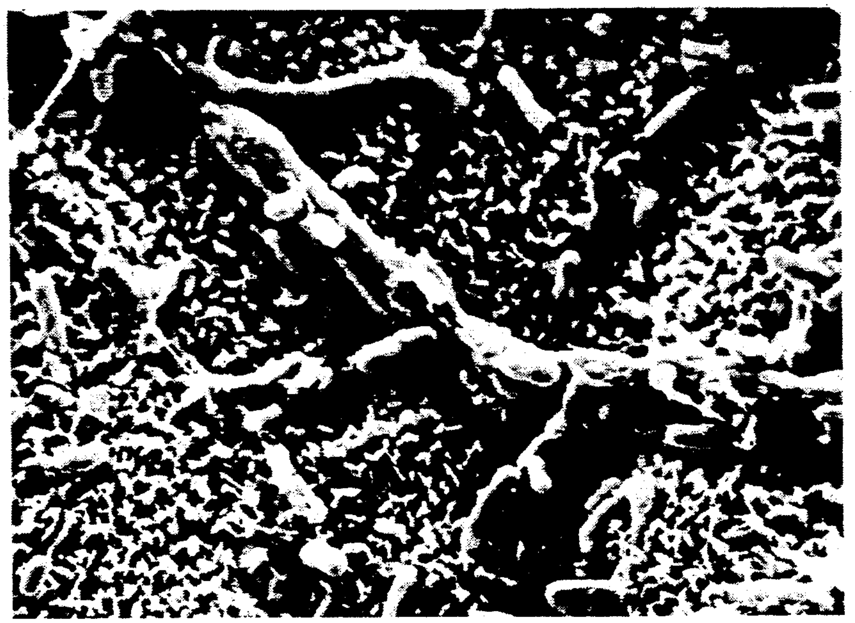
FIG. 8 shows a scanning electron micrograph of abnormal, pitted hypha colonized by *Bacillus cereus* on peanut leaf treated with I-chitin (industrial chitin) formulation+*Bacillus cereus* 5 days after application; 3,400X.
Figure 9:
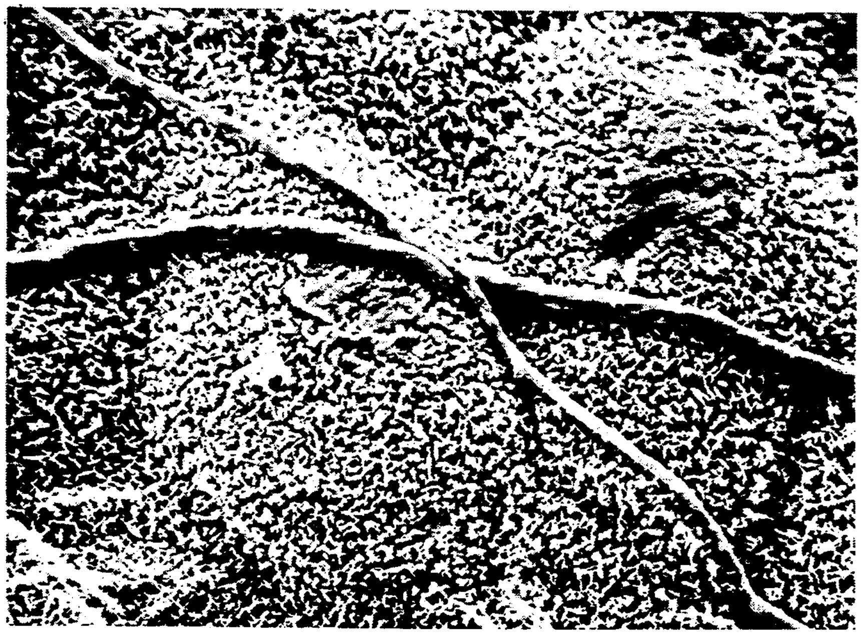
FIG. 9 shows a scanning electron micrograph of untreated peanut leaf surface with typical healthy fungal hypha; 2,000X.

Scanning electron micrographs of peanut leaves treated with the I-chitin formulation inoculated with *C. flaccumfaciens* showed typical Coryneform cells coionizing chitin in large numbers (FIG. 7). Further, they illustrated an altered surface topography where chitin had been applied. Colonization of I-chitin by applied *C. flaccumfaciens* and indigenous microorganisms also was apparent (FIG. 7), which indicated both growth (dividing cells) and metabolism of the substrate (fossil-like impressions on the chitin where cells had previously existed). Micrographs of chitin-treated, *B. cereus* inoculated leaves at five days after application revealed abnormally pitted fungal hyphae colonized by bacterial cells, some of which appeared to be dividing (FIG. 8), in contrast to untreated control leaves which were colonized by more typical fungal hyphae (FIG. 9).

These data indicate that the addition of applied biological control organisms along with a selectively available metabolic amendment (chitin) results in improved survival of the organisms and increased antagonism to pathogens. This benefit appears to arise through chitin utilization as a metabolic amendment and by improved environment for indigenous and applied organisms.

Example 4: Effect of Cellulose and Chitin on a Fungal Antagonist of an Apple Pathogen Introduction Andrews et al. (1983) screened 50 microorganisms isolated from the apple phyllosphere for antagonism to *Venturia inaequalis*. These were then ranked according to efficacy based on three in vitro and three in vivo tests: growth on nutrient agar, germination, and germ tube lengths on agarose-coated slides; and lesion size, overall symptom development, and conidial production on infected leaves. The best and most consistently antagonistic organism was *C. globosum.*

The severity of apple scab was consistently reduced by up to 90% in growth chamber studies when *C. globosum* ascospores are applied to apple seedlings along with conidia of the pathogen, *V. inaequalis* (Andrews et al., 1983). However, frequent field applications over three seasons reduced disease by only 0–25% (Boudreau and Andrews, 1987). The method of antagonism of *c. globosum* to *V. inaequalis* and other pests is suspected to be antibiosis. Although *Chaetomium globosum* has been used effectively in small field trials as a biological control agent against seedling blights, seed rots, and the bean seed fly, it has failed to exhibit effective and sustained apple scab suppression outside of controlled environments. This failure is typical of past foliar disease biological control work in general. This example utilizes the same host and antagonist to determine if results can be improved with the polymer food base technology.

Methods

Acid Hydrolysis of Cellulose

Powdered cellulose (Celufil, non-nutritive bulk, United States Biochemical Corporation) was mixed with phosphoric acid (85%, Fisher brand, ACS grade) in a blender using a high-speed setting at a concentration of approximately 25 g of cellulose per 1.0 liters of acid (unpublished method of R. Rodriguez-Kabana). The resultant suspension was allowed to stand at room temperature for 30 minutes with intermittent stirring. Then the acid-cellulose mixture was placed in a 115 liter plastic garbage can with roughly 95 l of tap water. The contents of the garbage can were then stirred, and the hydrolyzed-cellulose precipitate was allowed to settle. When the supernatant was clear, it was siphoned off, and the garbage can was refilled with water and stirred vigorously. This process of siphoning and refilling was repeated several times to "wash" the hydrolyzed cellulose and raise the pH toward neutral.

When the pH reached about 6.0, the supernatant was drained, and the cellulose sediment that remained was blended at high speed for several minutes to disintegrate any clumps. The suspension was strained using a 25 mesh screen, resuspended in excess distilled water, and allowed to settle. When the supernatant became clear, it was decanted, and the remaining liquid suspension was conserved as the final product.

Fungal Culture and Spore Production

*Chaetomium globosum* strain NRRL 6296 was selected for use in this experiment because of its demonstrated suppressive activity through the production of antifungal compounds to the apple scab pathogen, *Venturia inaequalis* (Boudreau and Andrews, 1987), and its rapid and abundant sporulation. Permanent cultures of *C. globosum* were maintained on lactic acid acidified potato dextrose agar (pH=4.5) and cellulose agar.

Cellulose agar was prepared by mixing 500 ml of 0.5% hydrolyzed cellulose suspension with 500 ml of tap water. To this mixture, 1.0 g potassium nitrate, 0.5 g potassium phosphate (dibasic), 0.2 g magnesium sulfate, and 30 g agar were added. The resultant solution was autoclaved and poured 0.5 cm deep into 8"×12"×4" alcohol-sterilized plastic cake pans, inoculated with *C. globosum* ascospores, and sealed with alcohol-sterilized plastic lids. These culture flats were incubated at 23° C. in sterile plastic garbage bags.

Preliminary Tests

Preliminary tests were conducted on the ability of *C. globosum* to grow on cellulose or chitin as a sole carbon source. This was done by inoculating petri dishes of 0.25% cellulose agar, 0.25% chitin agar, or water agar with *C. globosum* ascospores. These dishes were monitored over 14 days for sporulation and hyphal growth. The cellulose and chitin agar plates were also monitored for cleared zones indicating hydrolysis of the carbon source around the *C. globosum* colonies.

Field Tests

Field tests were designed to evaluate the possibility of biologically controlling apple scab (*Venturai inaequalis*), flyspeck (*Zygophiala jamaicensis*), and sooty blotch (*Gleodes pomigena*) with *Chaetomium globosum.*

The biological disease control properties of *Chaetomium globosum* were evaluated on trellised Early Red One apples on M26 rootstock at the North Alabama Horticultural Station, Cullman, Alabama. Thirty-six trees were arranged into four replicates, which each contained nine treatments: (1) chitin+*C. globosum*+N-acetylglucosamine (NAG)+Soydex, (2) chitin+-NAG+Soydex, (3) cellulose+cellobiose+*C. globosum*+Soydex, (4) cellulose+cellobiose+Soydex, (5) *C. globosum*+Soydex, (6) Soydex, (7) untreated, (8) benomyl 50W (Benlate, du Pont, 1.19 kg/kl)+captan 50W (Chevron, 4.78 Kg/Kl)+Soydex, (9) *C. globosum.* All concentrations of cellulose, chitin, Soydex were 0.5% (w/v, w/v, and v/v, respectively). Fertilization and insect control of apple trees were administered following the current industry standards.

All treatments were applied with 4 liter, hand-pumped tank sprayers to one-half of each tree; the treated half of each tree constituted one plot, and the untreated halves acted as buffers between treatments. Treatments receiving an organic amendment and *C. globosum* spores were sprayed twice on each spray date: Once with *C. globosum* plus Soydex and once with the organic amendment plus Soydex. This increased control over the concentration of *C. globosum* spores applied.

Treatments began when the apple leaves emerged in the spring (April 4) and were reapplied every seven days. This schedule was maintained for five weeks (until May 5), after which treatments were applied three times on a 14-day schedule until the trees reached terminal bud (June 16). Thereafter, applications were made every 21 days until the test termination on Aug. 3.

Plots were treated on the following dates: Apr. 4, Apr. 14, Apr. 21, Apr. 28, May 5, May 19, Jun. 2, Jun. 6, and Jul. 7. Mean daily maximum temperatures, mean daily average temperatures, and mean daily average rainfall data were collected throughout the season.

Samples of 25 apple fruits were collected from each of the 36 plots on Aug. 8, 1988, and rated for sooty mold (*Gloeodes pomigena*) and flyspeck (*Zygophiala jamaicensis*) infection. Sooty mold was subjectively rated on a scale from 0.0 to 3.0: 0.0 represented no visible infection, 1.0 represented a light infection on some fruits, 2.0 represented a heavy infection on some fruits with most fruits infected to some extent, and 3.0 represented a heavy infection on all fruits. Flyspeck levels were determined by counting the number of flyspeck infection loci or patches on each apple fruit.

Inoculum Survival and Growth

Leaf samples were randomly collected from 12 of the 36 plots on Apr. 28 immediately after treatments were applied for the fourth time. The 12 sampled plots were four replicates from the following treatments: cellulose +cellobiose+Soydex, *C. globosum*+Soydex, and cellulose +cellobiose+*C. globosum*+Soydex. A small cork borer was used to randomly collect three 0.5 cm leaf disks from three different leaves from each plot sample. This ensured adequate sample representation and uniform sample size which facilitated more accurate comparisons among treatments. These leaf disks were then prepared for scanning electron microscopy which provided visual evidence of, and allowed for a subjective rating of, *C. globosum* survival and colonization of the leaf surface; any colonization would be from the first three treatment applications. The subjective rating scale was between 0.0 and 4.0: 0.0 represented no *C. globosum* growth, 1.9 represented very few short hyphal strands visible on the leaf surface, 2.0 represented a few long hyphal strands and a moderate complement of short strands visible on the leaf surface, 3.0 represented many long hyphal strands and many short hyphal strands visible on the leaf surface, and 4.0 represented a hyphal mat covering the leaf surface.

Results

Preliminary Tests

Greenhouse experimentation demonstrated that 0.5% cellulose (w/v) with 0.5% Soydex (v/v) provided the best leaf coverage and amendment tenacity to apples. It was also determined that the most complete coverage was achieved by spraying plants to near runoff.

Evaluations of culture media demonstrated that *Chaetomium globosum* was capable of limited hyphal growth but with abundant sporulation when given either 0.25% hydrolyzed cellulose or 0.25% hydrolyzed chitin as a sole carbon source in a 2.0% agar medium. The fungus produced virtually no hyphae and did not sporulate when transferred to water agar plates. Chaetomium colonies produced cleared zones in both the chitin and cellulose agar.

Inoculum Survival and Growth

Figure 10:
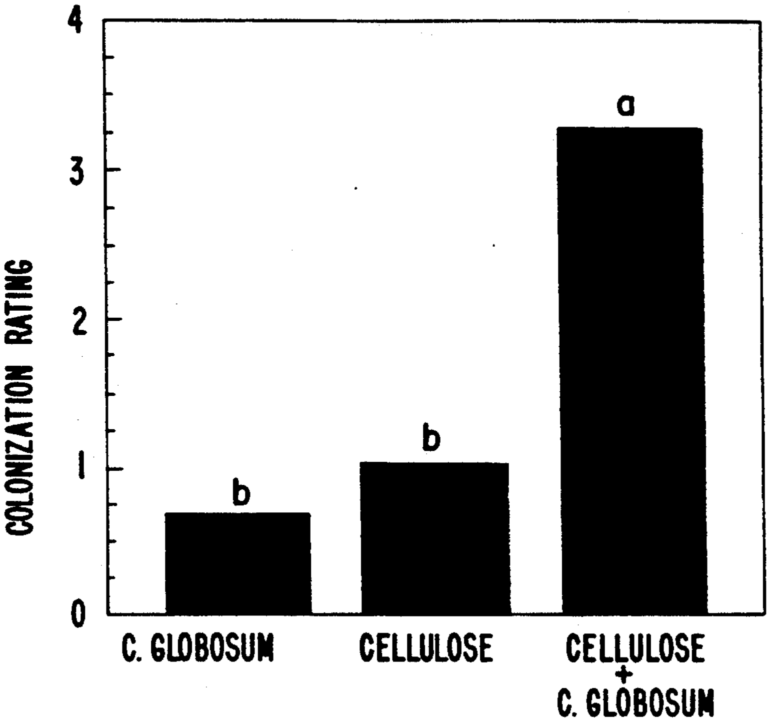
FIG. 10 shows cellulose alone and in combined formulation with *Chaetomium globosum* spores on the colonization by the fungus of apple leaf surfaces using scanning electron microscopy for visualization.

Scanning electron microscopy of the leaf disks clearly showed that *C. globosum* was extensively colonizing the cellulose deposits on the leaf surfaces seven days after the fourth treatment application. Subjective evaluations of leaf disks revealed that plots receiving only *C. globosum* ascospores+Soydex had very limited Chaetomium growth or colonization of the leaf surface. Plots receiving only cellulose (FIG. 10) had a higher colonization rating than plots receiving only *C. globosum* ascospores, but this increase was not statistically significant. This may indicate that there was a natural background of *C. globosum* since uninoculated plots had *C. globosum* growth, or it may indicate that a low level of inoculum spray drift occurred. The plots receiving both cellulose and *C. globosum* spores had a higher colonization rating than either of the other two treatments (alpha=0.05). No other cellulolytic or chitinolytic organisms were detected.

Field Tests

Figure 11:
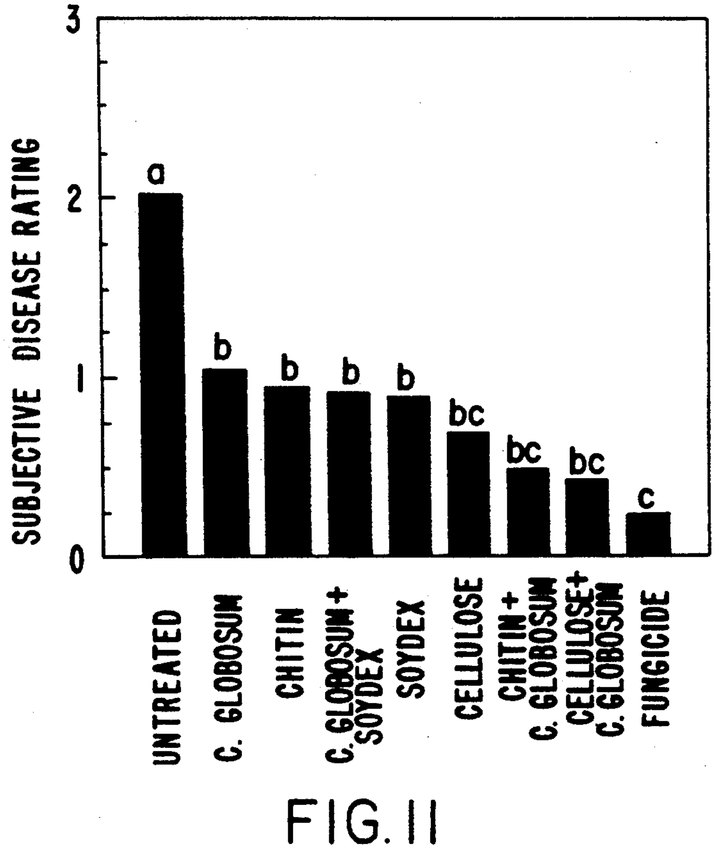
FIG. 11 shows biological control of sooty mold of apple fruits by *Chaetomium globosum* as affected by the addition of nutrient polymers.

When apples collected from each plot were subjectively rated for sooty mold disease levels (FIG. 11), untreated samples had the highest rating and were significantly different from all other treatments. Fungicide-treated plots had the lowest level of disease. However, soydex did suppress sooty mold, reducing disease by more than 50 percent. Therefore, the level of disease suppression provided by each treatment is partially due to Soydex, except in the case of *C. globosum* ascospores alone, which contained no Soydex.

Figure 12:
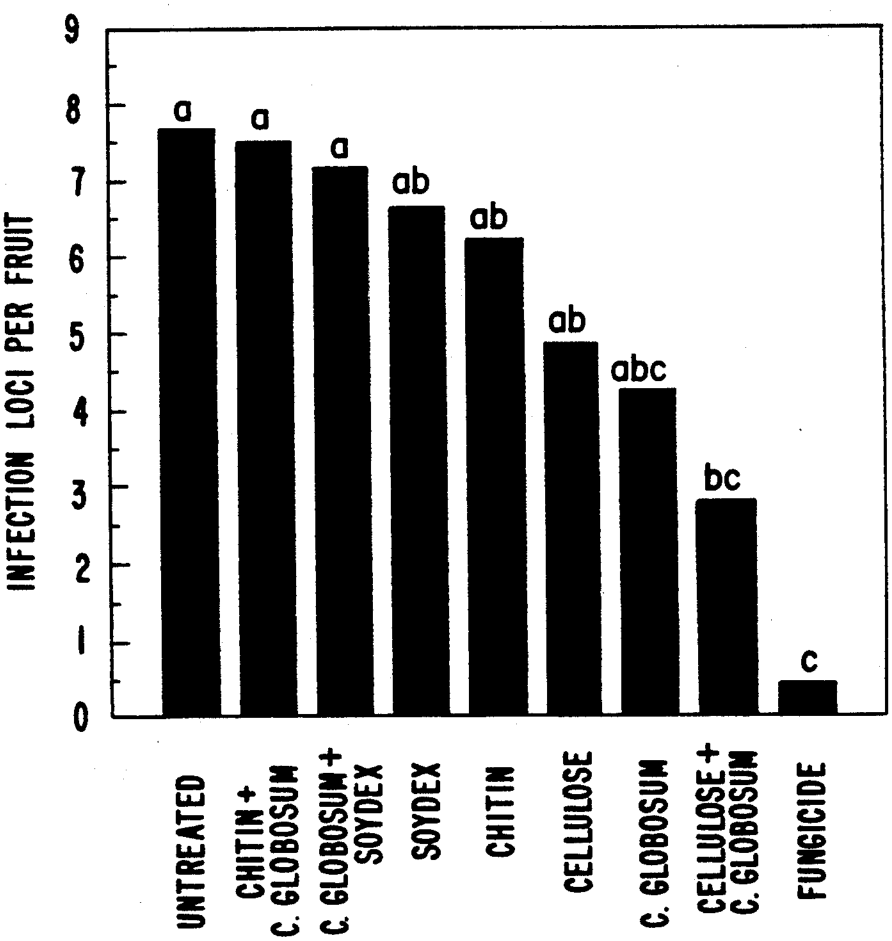
FIG. 12 shows biological control of flyspeck of apple fruits by *Chaetomium globosum* as affected by the addition of nutrient polymers.

The number of flyspeck infection loci per fruit (FIG. 12) shows that cellulose along significantly reduced disease (alpha=0.10) by 36% over the untreated control, cellulose+*C. globosum* reduced disease by 63%, and the fungicide reduced disease by the greatest margin, 93%.

Discussion

The addition of cellulose with *Chaetomium globosum* ascospores greatly enhanced Chaetomium growth. This increase could be due to the creation of physical environments that provided microclimates favorable for *C. globosum* growth and/or the utilization of cellulose as a food base.

Cellulose and chitin both adhered well to the apple foliage and fruit, and both amendments were suppressive to fruit disease when applied either with without *C. globosum* ascospores. When cellulose was applied with *C. globosum*, the principal mode of disease suppression was probably antibiosis. This is supported by the observation (from microscopy and leaf-wash dilution-plating) that *C. globosum* nearly eliminated the indigenous microflora.

The observation that *C. globosum* alone was not suppressive to either flyspeck or sooty blotch is similar to the results reported by Boudreau and Andrews (1987) in which *C. globosum* alone failed to reduce apple scab in field tests.

Subjective ratings of sooty blotch on field grown apples confirmed this suppression and suggested additive control and possibly synergism between the amendments and *C. globosum*. This control was especially apparent in the flyspeck infection loci counts where cellulose+*C. globosum* exhibited excellent flyspeck suppression.

The control exhibited by cellulose+*C. globosum* indicated that the concept of selectively enhancing the growth of a suppressive organism through the creation of physical environments and through the provision of nutrients was practical.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

References

Andrews, J.H., Berbee, F.M., and Nordheim, E.V. 1983. Microbial antagonism to the imperfect stage of the apple scab pathogen, *Venturia inaequalis*. Phytopathology 73:228-234.

Bailey, J.E. and Spurr, H.W. 1984. Evaluation of two biological control organisms for early leafspot control of peanut, 1982. Fungic. Nematic. Tests 39:132.

Baker, K.F. and Cook, R.J. 1974. Biological Control of Plant Pathogens. W.H. Freeman and Co., San Francisco, Cal. 433 pp.

Bashi, E. and Fokkema, N.J. 1977. Environmental factors limiting growth of *Sporobolomyces roseus*, an antagonist of *Cochliobolus sativus* on wheat leaves. Trans. Br. Mycol. Soc. 68:17-25.

Bird, A.F. and McClure, M.A. 1976. The tylenchoid (nematoda) egg shell. Structure, composition and permeability. Parasitology 72:19-28.

Blakeman, J.P. 1985. Ecological succession of leaf surface microorganisms in relation to biological control. Pages 6-30 in: Biological Control on the Phylloplane. C.E. Windel and S.E. Lindow, eds. American Phytopathological Society, St. Paul, Minn.

Boudreau, M.A. and Andrews, J.H. 1987. Factors influencing antagonism of *Chaetomium globosum* to *Venturia inaequalis*: A case study in failed biocontrol. Phytopathology 77:1470-1475.

Brown, L.R., Blasingame, D.J., Ladner, C.M., Teichert, C., and Brown, S. 1979. The use of chitinous seafood wastes for the control of plant parasitic nematodes. Report Bureau of Marine Resources. Mississippi Department of Wildlife Conservation. 42 pp.

Burchill, R.T. and Cook, R.T.A. 1971. The interactions of urea and microorganisms in suppressing the development of perithecia of *Venturia inaequalis* (Cke) Wint. Pages 471-483 in: Ecology of Leaf Surface Microorganisms. T.F. Preece and C.H. Dickinson, eds. Academic Press, London.

Chet, I., Cohen, E., and Elster, I. 1986. The role of chitinase and chitin synthetase inhibitors in controlling plant pathogenic fungi. Pages 237-240 in: Chitin in Nature and Technology. Plenum Press, N.Y. 583 pp.

Danilewicz, K. 1980. Studies on the epiphytic bacteria on *Populus alba* L. at the time of optimal and minimal cambium activity and infection by Venturia. Eur. J. For. Pathol. 10:296-306.

Godoy, G., Rodriguez-Kabana, R., and Morgan-Jones, G. 1982. Parasitism of eggs of *Heterodera glycines* and *Meloidogyne arenaria* by fungi isolated from cysts of *H. glycines*. Nematropica 12:111-119.

Godoy, G., Rodriguez-Kabana, R., Shelby, R.A., and Morgan-Jones, G. 1983. Chitin amendments for control of *Meloidogye arenaria* in infested soil. II. Effects on microbial population. Nematropica 13:63-74.

Gullino, M.L. and Garibaldo, A. 1986. Biological and integrated control of gray mould of grape in Italy. (Abstr.) Phytopathology 76:1064.

Jimenez, J.M., Galindo, J.J., and Ramirez, C. 1986. Studies on biological control of *Monilia roreri* by epiphytic bacteria. (Abstr.) Phytopathology 76:1118.

Knudsen, G.R. and Hudler, G.W. 1984. Interactions between epiphytic bacteria and conidia of *Gremmeniella abientine*. Pages 217-225 in: Scleroderris Canker of Conifers. P.D. Manion, ed. Nijhoff/Junk, The Hague, The Netherlands.

Knudsen, G.R. and Spurr, H.W. 1987. Field persistence and efficacy of five bacterial preparations for control of peanut leaf spot. Plant Dis. 71:442-445.

Leben, C. and Daft, G.C. 1965. Influence of an epiphytic bacterium on cucumber anthracnose, early blight of tomato, and northern leaf blight of corn. Phytopathology 55:760-762.

Leben, C., Daft, G.C., Wilson, J.D., and Winter, H.F. 1965. Field tests for disease control by an epiphytic bacterium. Phytopathology 55:1375-1376.

Lindow, S.E. 1983. Methods of preventing frost injury caused by epiphytic ice-nucleation-active bacteria. Plant Disease 67:327-333.

Lopez-Romero, E. and Ruiz-Herera, J. 1986. The role of chitin in fungal growth and morphogenesis. Pages 55-62 in: Chitin in Nature and Technology. R. Muzzarelli, C. Jeuniaux, and G.W. Gooday, eds. Plenum Press, N.Y. 583 pp.

McCandliss, R.J., Eastwood, B.J., and Milch, R.A. 1985. Nematocidally active chitin-protein complex. U.S. Pat. No. 4,536,207.

Mian, I.H., Godoy, G., Shelby, R.A., Rodriguez-Kabana, R., and Morgan-Jones, G. 1982. Chitin amendments for control of *Meloidogyne arenaria* in infested soil. Nematropica 12:71-84.

Mitchell, R. and Alexander, M. 1962. Microbial processes associated with the use of chitin for biological control. Soil Sci. Soc. Am. Proc. 26:556-558.

Morgan-Jones, G. and Rodriguez-Kabana, R. 1981. Fungi associated with cysts of *Heterodera glycines* in Alabama soil. Nematropica 11:69-77.

Morris, C.E. and Rouse, D.I. 1985. Role of nutrients in regulating epiphytic bacterial populations. Pages 63-82 in: Biological Control on the Phylloplane. C.E. Windels and S.E. Lindow, eds. American Phytopathological Society, St. Paul, Minn.

Ordentlich, A., Elad, Y., and Chet, I. 1988. The role of chitinase of *Serratia marcescens* in biocontrol of *Sclerotium rolfsii*. Phytopathology 78:84-88.

Ownley-Gintis, B., Morgan-Jones, G., and Rodriguez-Kabana, R. 1982. Mycoflora of young cysts of *Heterodera glycines* in North Carolina soils. Nematropica 12:295-303.

Rodgers, P.B. 1989. Potential of Biological Control Organisms as a Source of Antifungal Compounds for Agrochemical and Pharmaceutical Product Development. Pestic. Sci. 27:155-164.

Rodriguez-Kabana, R., Godoy, G., Morgan-Jones, G., and Shelby, R.A. 1983. The determination of soil chitinase activity. Conditions for assay and ecological study. Plant and Soil 75:95-106.

Rytter, J.R. and Lukezic, F.L. 1986. Biological control of geranium rust by a bacterial antagonist. (Abstr.) Phytopathology 76:1134.

SAS Institute, Inc., SAS User's Guide: Statistics, Version 5 Edition, Cary, North Carolina: SAS Institute, Inc., 1985.

Smith, D.H. 1984. Pages 5-7 in: Compendium of Peanut Diseases. D.M. Porter, D.H. Smith, and R. Rodriguez-Kabana, eds. American Phytopathological Society, St. Paul, Minn.

Spurr, H.W., Jr. 1981. Experiments on foliar disease control using bacteria antagonists. Pages 369-381 in: Microbial Ecology of the Phylloplane. J.P. Blakeman, ed. Academic Press, London.

Veldkamp, H. 1955. Aerobic decomposition of chitin by microorganisms. Meded. Landbouw., Wageningen 55:127–174.

Warren, R.C. 1972. Interference by common leaf saprophytic fungi with the development of *Phoma beta* lesions on sugarbeet leaves. Ann. Appl. Biol. 72:137–144.

What is claimed is:

1. A method of controlling the population of a first microorganism at a foliar locus by preferentially enhancing the population of a second microorganism at said locus, comprising applying to the locus an amount of a durable, substantially water-insoluble polymeric substrate having a solubility in water (20° C. of at most 1% which has been selected for being preferentially biodegraded by said second microorganism, whereby growth of said second microorganism is substantially preferential to that of said first microorganism, and wherein said polymeric substrate is applied in admixture with a binder which increases its durability.

2. A method of claim 1, further comprising applying an inoculum of the second microorganism to said locus.

3. A method of claim 1, wherein the durability of the polymeric substrate at the foliar locus is at least 2 weeks.

4. A method of claim 1, wherein the polymeric substrate is a polysaccharide, a protein or a mixture thereof.

5. A method of claim 4, wherein the polymeric substrate is cellulose, chitin, carrageenan, a $\beta$-1,3-glucan, or poly(galacturonic acid), or a mixture thereof.

6. A method of claim 5, wherein the polymeric substrate is chitin or cellulose.

7. A method of claim 1, wherein the second microorganism is *Bacillus subtilis, Bacillus cereus, Curtobacterium flaccumfaciens* or *Chaetomium globosum*.

8. A method of claim 1, wherein the second microorganism is endogenous.

9. A method of claim 1, wherein the binder is a drying oil.

10. A method of controlling the population of a first microorganism at a foliar locus by preferentially enhancing the population of a second microorganism at said locus, comprising applying to the locus an amount of a durable, substantially water-soluble polymeric substrate having a solubility in water (20° C.) of at most 1% effective as a selective habitat enhancer which has been selected for substantially preferentially potentiating growth of said second microorganism with respect to said first microorganism, and wherein said polymeric substrate is applied in admixture with a binder which increases its durability.

11. A method of claim 10, wherein the polymeric substrate is applied in admixture with a binder which increases its durability.

12. A method of claim 10, wherein the habitat modifier functions by provision of a selective physical environment for said second microorganism.

13. A method of claim 10, further comprising applying an inoculum of the second microorganism to said locus.

14. A method of claim 10, wherein the polymeric substrate is cellulose.

15. A method of claim 13, wherein the second microorganism is *Bacillus subtilis, Bacillus cereus, Curtobacterium flaccumfaciens* or *Chaetomium globosum*.

16. A method of enhancing the population of a microorganism at a foliar locus, comprising applying to the locus and amount of a substantially water-insoluble polymeric substrate having a solubility in water (20° C.) of at most 1% which has been selected for being effective as a durable, selective habitat enhancer which potentiates growth of said microorganism, and wherein said polymeric substrate is applied in admixture with a binder which increases its durability.

17. A method of claim 16, wherein the habitat modifier functions by provision of a protective physical environment for said microorganism.

18. A method of claim 16, wherein the polymeric substrate is biodegraded by the microorganism.

19. A method of claim 6, wherein the polymeric substrate is chitin which has been hydrolyzed to a weight average molecular weight of from 4000 to 10,000 daltons.

20. A method of claim 9, wherein the polymeric substrate is chitin.

* * * * *